United States Patent
Moga et al.

(10) Patent No.: US 11,622,750 B2
(45) Date of Patent: *Apr. 11, 2023

(54) METHODS FOR DELIVERY OF BODILY FLUIDS ONTO A FIBROUS SUBSTRATE

(71) Applicant: Tasso, Inc., Seattle, WA (US)

(72) Inventors: Ben Moga, Soquel, CA (US); Ben Casavant, Seattle, WA (US); Erwin Berthier, Seattle, WA (US)

(73) Assignee: Tasso, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/186,483

(22) Filed: Feb. 26, 2021

(65) Prior Publication Data

US 2021/0177383 A1    Jun. 17, 2021

Related U.S. Application Data

(63) Continuation of application No. 15/711,746, filed on Sep. 21, 2017, now Pat. No. 11,523,805.

(Continued)

(51) Int. Cl.
*A61B 10/00*  (2006.01)
*A61B 5/15*  (2006.01)
*B01L 3/00*  (2006.01)

(52) U.S. Cl.
CPC .... *A61B 10/0045* (2013.01); *A61B 5/150022* (2013.01); *A61B 5/150068* (2013.01); *A61B 5/150251* (2013.01); *A61B 5/150343* (2013.01); *A61B 5/150366* (2013.01); *A61B 10/0038* (2013.01); *A61B 10/0096* (2013.01);

(Continued)

(58) Field of Classification Search
CPC .......... A61B 10/0045; A61B 5/150068; A61B 5/150343; A61B 5/150366; A61B 10/0096; A61B 10/0038; A61B 5/150251; A61B 2503/42; A61B 5/150022; B01L 2400/0406; B01L 3/502; B01L 3/5023;

(Continued)

(56) References Cited

U.S. PATENT DOCUMENTS 6,226,378 B1    5/2001  Quattrocchi
11,523,805 B2    12/2022  Moga et al.
(Continued)

FOREIGN PATENT DOCUMENTS

CN    102576031    7/2012
CN    104582571 A    4/2015
(Continued)

OTHER PUBLICATIONS

Chinese First Office Action issued for Chinese Application No. 201780072026.9; Applicant: Tasso, Inc., dated Mar. 26, 2021, 7 pages.

(Continued)

*Primary Examiner* — Rebecca M Fritchman
(74) *Attorney, Agent, or Firm* — Perkins Coie LLP

(57) ABSTRACT

The disclosed apparatus, systems and methods relate to devices, systems and methods for the collection of bodily fluids. The collector can make use of microfluidic networks connected to collection sites on the skin of a subject to gather and shuttle blood into a removable cartridge. The collected fluid is supplied to substrate for drying, storage and transport.

19 Claims, 22 Drawing Sheets

Related U.S. Application Data

(60) Provisional application No. 62/397,751, filed on Sep. 21, 2016.

(52) U.S. Cl.
CPC ............ B01L 3/502 (2013.01); B01L 3/5023 (2013.01); *A61B 2503/42* (2013.01); *B01L 2200/18* (2013.01); *B01L 2300/069* (2013.01); *B01L 2300/0816* (2013.01); *B01L 2400/0406* (2013.01)

(58) Field of Classification Search
CPC ........... B01L 2200/18; B01L 2300/069; B01L 2300/0816
See application file for complete search history.

(56) References Cited

U.S. PATENT DOCUMENTS

| | | | |
|---|---|---|---|
| 2001/0021536 A1* | 9/2001 | Lee ..................... | G01N 33/558 436/518 |
| 2004/0197226 A1 | 10/2004 | Ray et al. | |
| 2005/0288605 A1* | 12/2005 | Pellegrino ........... | A61B 10/025 600/565 |
| 2008/0243159 A1 | 10/2008 | Schraga | |
| 2009/0287237 A1 | 11/2009 | Nicholls | |
| 2011/0124130 A1* | 5/2011 | Wagner ................ | G01N 33/558 422/400 |
| 2013/0211289 A1* | 8/2013 | Moga ............... | A61B 5/150412 600/578 |
| 2014/0208836 A1* | 7/2014 | Murphy ................ | G01N 30/06 73/61.55 |
| 2015/0080929 A1 | 3/2015 | Yi et al. | |
| 2015/0209068 A1 | 7/2015 | Booker et al. | |
| 2015/0305916 A1 | 10/2015 | Hanuka et al. | |
| 2016/0331292 A1 | 11/2016 | Leskowich et al. | |
| 2022/0395620 A1 | 12/2022 | Peterson et al. | |

FOREIGN PATENT DOCUMENTS

| | | |
|---|---|---|
| CN | 104968269 A | 10/2015 |
| EP | 1389443 | 2/2004 |
| EP | 2439540 | 4/2012 |
| EP | 2484448 | 8/2012 |
| EP | 2863798 | 4/2015 |
| WO | WO2013191552 | 12/2013 |
| WO | WO2014088606 | 6/2014 |
| WO | WO2016074046 | 5/2016 |
| WO | WO2021076846 | 4/2021 |

OTHER PUBLICATIONS

Extended European Search Report received for EP Application No. 17853907.8; Applicant: Tasso, Inc, dated Apr. 9, 2020, 8 pages.

International Preliminary Report on Patentability received for PCT Application No. PCT/US2017/052754; Applicant: Tasso, Inc., dated Apr. 4, 2019, 7 pages.

International Search Report and Written Opinion received for PCT Application No. PCT/US17/52754; Applicant: Tasso, Inc., dated Nov. 29, 2017, 12 pages.

International Search Report and Written Opinion received for PCT Application No. PCT/US20/55916; Applicant: Tasso, Inc., dated Mar. 18, 2021, 11 pages.

\* cited by examiner

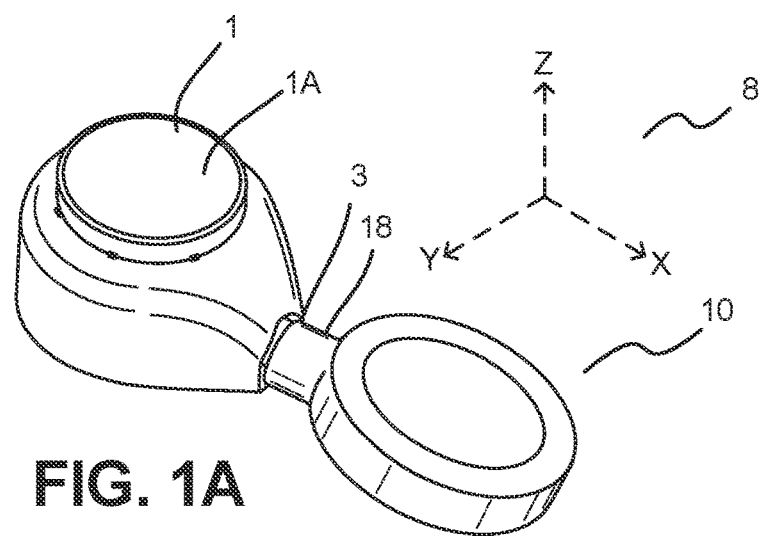
FIG. 1A
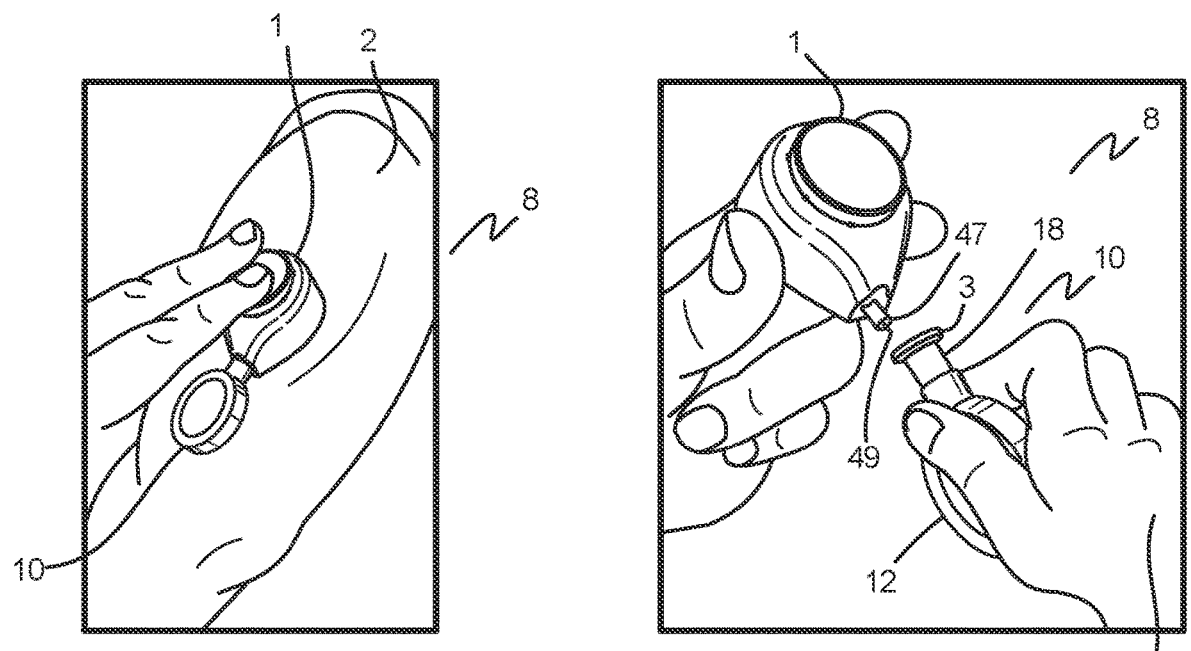
FIG. 1B
FIG. 1C
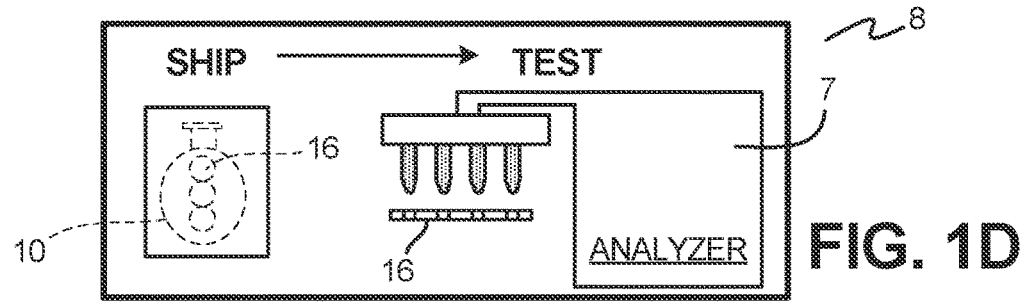
FIG. 1D

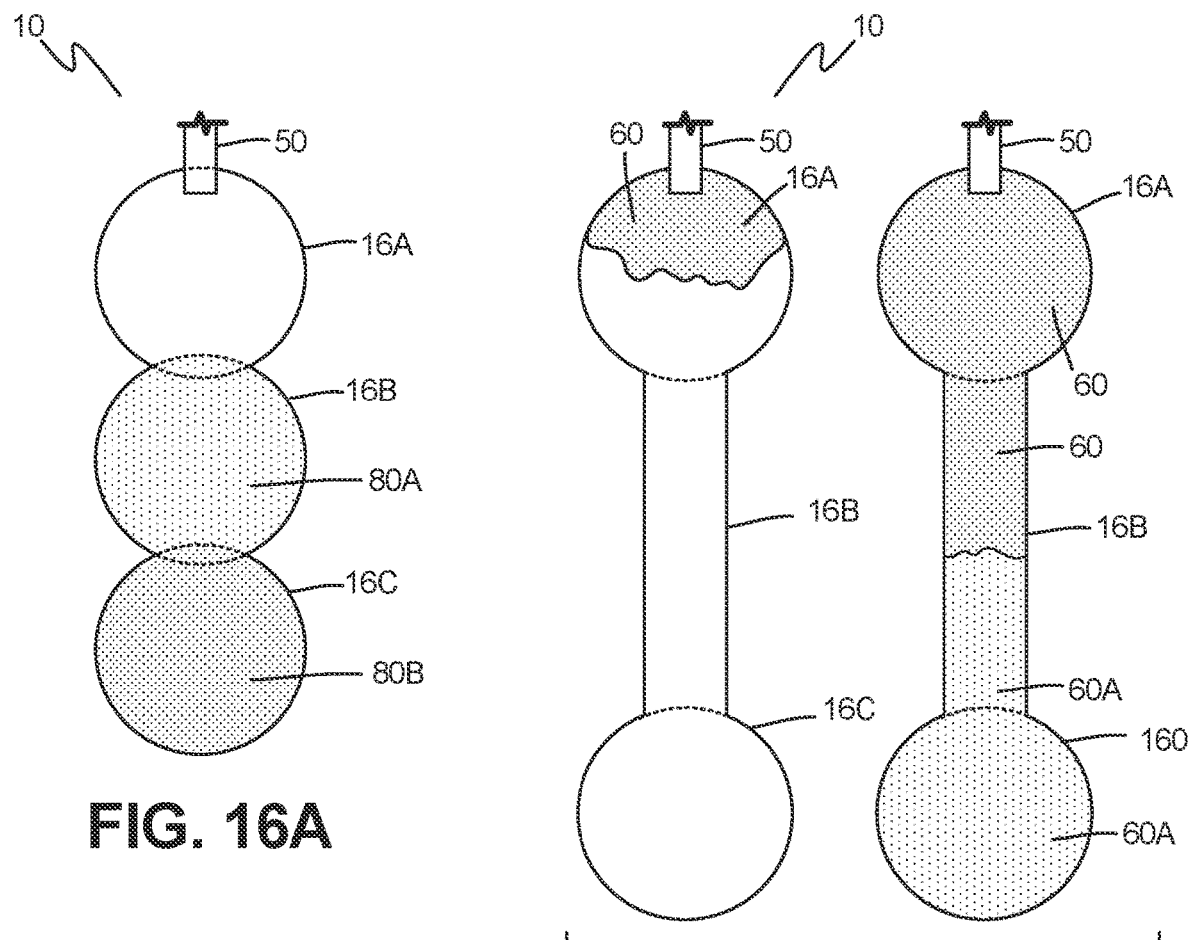
FIG. 16A
FIG. 16B
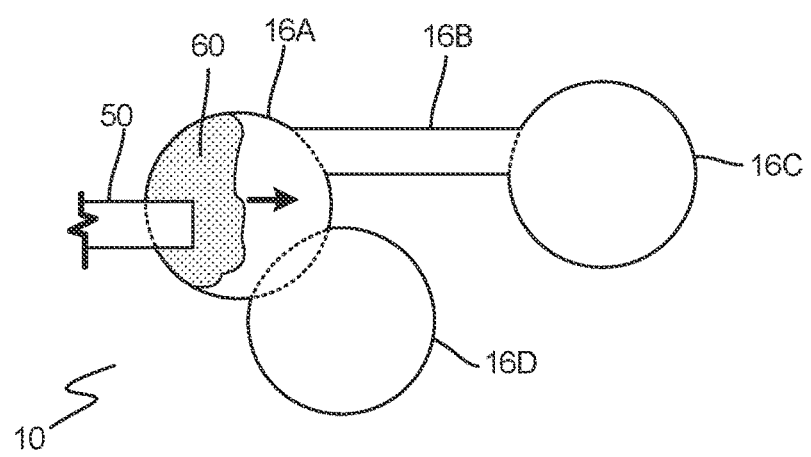
FIG. 16C

METHODS FOR DELIVERY OF BODILY FLUIDS ONTO A FIBROUS SUBSTRATE

CROSS-REFERENCE TO RELATED APPLICATIONS

This application is a continuation of U.S. patent application Ser. No. 15/711,746, filed on Sep. 21, 2017, and titled "METHODS FOR DELIVERY OF BODILY FLUIDS ONTO A FIBROUS SUBSTRATE," which claims priority to U.S. Provisional Patent Application No. 62/397,751, filed on Sep. 21, 2016, and titled "METHODS FOR DELIVERY OF BODILY FLUIDS ONTO A FIBROUS SUBSTRATE," each of which is herein incorporated by reference in its entirety.

FEDERALLY SPONSORED RESEARCH OR DEVELOPMENT

This invention was made with government support under Award #1 R44 AI122474-01 from the Department of Health and Human Services of National Institutes of Health (NIH). The government has certain rights in the invention.

TECHNICAL FIELD

The disclosed technology relates generally to the collection of bodily fluids, and in particular, to the devices, systems, and methods providing for the collection, storage, dying and delivery of fluids in fibrous matrices or substrates. In particular, the devices, systems and methods disclosed here pertain to the delivery of blood or other bodily fluids onto substrates such as paper or fiber matrices in controllable volumes, the drying of blood onto the matrices, and the ability to transport the samples safely to remote analysis locations. These embodiments have implications for clinical relevance of capillary blood collection, safety, and manufacturing.

BACKGROUND

Devices, systems and methods to collect bodily fluids are necessary devices for the growing field of personalized medicine. While analysis laboratories are well suited to perform diagnostic tests the collection of blood samples remains challenging, in particular for patients that do not have simple access to the blood testing laboratory. These patients can be located in rural areas, underserved sub-urban areas, or low resource areas and have significant barriers to accessing diagnostic services. In order to reach patients in any location and connect them with blood testing facilities; robust systems for sample encapsulation, stabilization, and shipping must be developed.

Thus, there is a need in the art for improved methods that allows blood transfer from capillary collection systems onto substrates that allow stabilization and transportation of the sample at ambient temperatures. Paper and fiber substrates have been utilized extensively to stabilize blood-based analytes such as viral RNA, antigens, and antibodies, and allow the transportation or bio-banking of blood samples. However, paper-based stabilization systems suffer from three main limitations: (1) the difficulty of transferring blood to the paper resulting in inconsistencies in the precision of the blood volumes and contamination of blood outside of the paper substrate, (2) the difficulty of quantifiably depositing and recuperating a known volume of blood, as the blood can wick into unpredictable shapes or suffer from variability in the placement, and (3) a challenge in handling and preparation of the imbibed paper for transportation, since contamination may still occur until the blood is actually dry.

Thus, there is a need in the art for improved microfluidic devices for fluid handling and transfer, and related systems and methods.

SUMMARY

Discussed herein are various embodiments of methods that allow the transfer of blood from blood collection devices onto paper matrices, the aliquotion of the blood into controlled volumes, and the drying of the blood on the matrix for robust transportation. For brevity, these embodiments may be described in relation to a "collector" and a "cartridge" though that is not intended to limit the scope of the disclosure in any way.

Example 1 the fluid collection system includes a fluid cartridge, including a housing including a lumen a connector; and at least one substrate disposed within the lumen, where the substrate is configured to be in fluidic communication with the connector so as to receive fluid from a fluid collection device.

In Example 2, the system of Example 1 wherein the housing includes a plurality of interlocking housing portions.

In Example 3, the system of Example 1 wherein the interlocking portions include interlocking projections.

In Example 4, the system of Example 1 wherein the housing includes a plurality of tabs configured to secure the at least one substrate within the lumen.

In Example 5, the system of Example 1 wherein the tabs are fixedly attached to the interlocking housing portions.

In Example 4, the system of Example 1 wherein the housing includes a gasket disposed between the interlocking housing portions.

In Example 5, the system of Example 1 wherein the housing includes a removable cover secured over an opening.

In Example 6, the system of Example 1 wherein the removable cover is secured to the housing via adhesive.

In Example 7, the system of Example 1 wherein the at least one fluidic channel is an open microfluidic channel.

In Example 8, the system of Example 1 wherein the housing includes a connector configured to attach to a fluid collection device.

In Example 8, the system of Example 1 wherein the cartridge further includes an inlet configured to receive fluid from the fluid collection device via the connector.

In Example 9, the system of Example 1 wherein the further including an overflow reservoir.

In Example 10, the system of Example 1 wherein the at least one substrate includes two or more substrates disposed adjacently.

In Example 11, the system of Example 1 wherein the at least one substrate includes two or more substrates disposed separately.

In Example 12, the system of Example 1 wherein the at least one substrate includes a plurality of subunits.

In Example 13, the fluid collection system of Example 1 where the at least one substrate includes at least one reagent.

In Example 13, the fluid collection system of Example 1 further including an inlet in fluidic communication with the fluid collection device and at least one substrate.

In Example 13, the fluid collection system of Example 1 wherein the housing includes at least one vent.

In Example 14, a fluid collection and storage cartridge, including an interlocking housing defining a lumen; at least one fluidic channel; and at least one substrate, where the at least one substrate is disposed within the lumen and in fluidic communication with the at least one fluidic channel.

In Example 15, the cartridge of Example 14 wherein the at least one fluidic channel is an open microfluidic channel.

In Example 16, the cartridge of Example 14 wherein the housing includes a connector configured to attach to a fluid collection device.

In Example 17, the cartridge of Example 14 wherein the cartridge further includes an inlet configured to receive fluid from the fluid collection device via the connector.

In Example 18, the cartridge of Example 14 further including an overflow reservoir.

In Example 19, the cartridge of Example 14 wherein the at least one substrate includes two or more substrates disposed adjacently.

In Example 20, the cartridge of Example 14 wherein the at least one substrate includes two or more substrates disposed separately.

In Example 21, the cartridge of Example 14 wherein the at least one substrate includes a plurality of subunits.

In Example 22, the cartridge of Example 14 wherein the at least one substrate includes at least one reagent.

In Example 23, the cartridge of Example 14 further including an inlet in fluidic communication with the fluid collection device and at least one substrate.

In Example 24, the cartridge of Example 14 wherein the housing includes at least one vent.

In Example 25, a fluid collection system, including a fluid collection device including at least one microfluidic channel; and a removable cartridge including a housing defining a lumen and containing at least one substrate, where the removable cartridge is configured to be detached from the fluid collection device for the drying and shipping of fluid contained by the at least one substrate.

In Example 26, the fluid collection system of Example 25 wherein the at least one substrate includes at least one reagent.

In Example 27, the fluid collection system of Example 25 further including an inlet in fluidic communication with the fluid collection device and at least one substrate.

In Example 28, the fluid collection system of Example 25 wherein the housing includes at least one vent.

In Example 29, a collector, comprises a housing that is placed onto the skin of the user and is able to collect blood and deliver it through a connector. The cartridge is appended to the collector through the connector and received the blood during the actuation of the collector. As blood is received by the cartridge it is dispatched onto a fibrous or paper substrate on which it can be dried. The cartridge may be detached for shipping simplicity.

Disclosed herein are various embodiments of an integrated collection and containment device that collects and transfers the bodily fluid from a subject's tissue into an easily detachable tube or reservoir. Previous technologies approached the transfer of the bodily fluid in a linear manner: one device enabled the bodily fluid to exit the tissue and another device was used to collect the bodily fluid. In contrast, the implementations disclosed herein simplify the process of bodily fluid collection by integrating the collection of the bodily fluid directly with the containment of bodily fluid within the same device.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 1A is a perspective view of the cartridge attached to a fluid collection device, according to one embodiment.

FIG. 1B is a perspective view of the device and cartridge of FIG. 1A placed on the skin of a patient.

FIG. 1C is a perspective view showing the detachment of the collector of FIG. 1A from the fluid collection device.

FIG. 1D is a schematic showing the transportation and analysis of fluid contained in the cartridge, according to one embodiment.

FIGS. 4B-1 through 4B-4 are exploded views of a cartridge having interlocking housing portions, according to another embodiment.

FIG. 16A is a top view of a series of treated substrates within the cartridge, according to one embodiment.

FIG. 16B is a side-by-side top view of an implementation of the substrates having preferential filling properties.

FIG. 16C is a top view of yet another implementation of the substrate disposed within the cartridge.

DETAILED DESCRIPTION

Figure 2A:
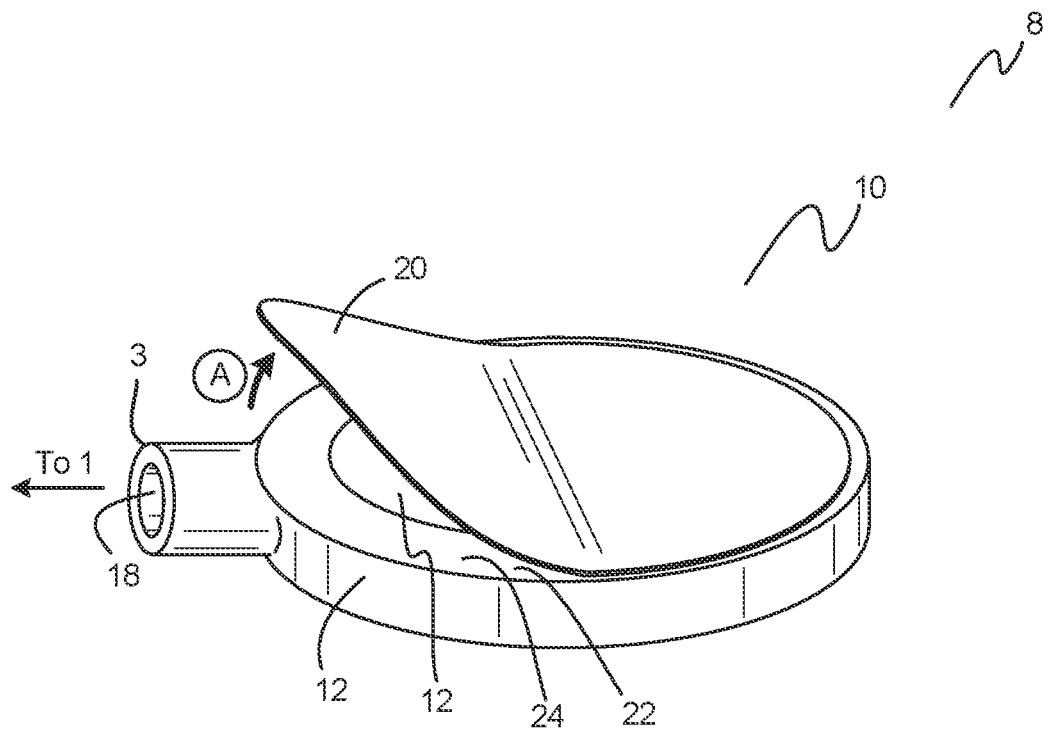
FIG. 2A is a perspective view of a collector containing paper matrices and an adhesive cover that can be removed to access the paper contained within, according to one adhesive.

The various embodiments disclosed or contemplated herein relate to a single device that can be used by untrained or minimally-trained persons to both collect bodily fluid and seamlessly deliver the sample onto a substrate, such as a paper or fiber matrix, for simple and robust transportation and stabilization of blood-based analytes. In various implementations, these embodiments allow for the sequential and measured collection of aliquots or fluid samples onto the substrate.

Disclosed herein are various embodiments of an integrated or modular fluid collection device that is able to collect and transfer the bodily fluid from a subject's tissue into an easily detachable cartridge or collector. In various implementations, the collector contains substrate(s) for the absorption and drying of the collected fluid, and can be detached from the fluid collection device for easy transport to an off-site laboratory. Previous technologies approached the transfer of the bodily fluid in a linear manner: one device enabled the bodily fluid to exit the tissue and another device was used to collect the bodily fluid. In contrast, the implementations disclosed herein simplify the process of bodily fluid collection by integrating the collection of the bodily fluid directly with the containment of bodily fluid within the same starting device.

An exemplary embodiment of the system 5 comprising a fluid collection device 1 and a fluid collector or cartridge 10 is shown in FIGS. 1A, 1B, 1C and 1D. In use, the device is used to puncture the skin of the subject and collect fluid, such as blood, which flows into the collector or cartridge 10 for storage and transport.

It is understood that the fluid collection devices 1 contemplated herein generally relate to devices, systems and methods for bodily fluids, such as those having an actuator—or "button"—at one end and at least one lancet disposed within the opposite end. In these implementations, when the button 1A is depressed, an actuation mechanism is deployed—lancets extend to pierce the skin of a subject 2 for the collection of fluid and transport of the fluid into the cartridge 10, such as via microfluidic channels disposed therein. For example, the various embodiments disclosed of the cartridge 1 disclosed herein may be incorporated into or used with any of the fluid collection devices and systems 1 disclosed in co-pending U.S. application Ser. No. 13/949,108, filed Jul. 23, 2013, entitled "Methods, Systems, and Devices Relating to Open Microfluidic Channels," which issued on Mar. 22, 2016 as U.S. Pat. No. 9,289,763, U.S. application Ser. No. 13/750,526, filed Jan. 25, 2013, entitled "Handheld Device for Drawing, Collecting, and Analyzing Bodily Fluid," U.S. application Ser. No. 14/816,994, filed Aug. 3, 2015, entitled "Devices, Systems and Methods for Gravity-Enhanced Microfluidic Collection, Handling and Transferring of Fluids," U.S. application Ser. No. 14/932,485, filed Nov. 4, 2015 and entitled "Methods, Systems, and Devices Relating to Open Microfluidic Channels," U.S. application Ser. No. 15/387,177, filed Dec. 21, 2016, entitled "Devices, Systems and Methods for Actuation and Retraction in Fluid Collection," and U.S. Application No. 62/533,323, filed Jul. 7, 2017 and entitled "Apparatus, Systems and Methods for Preparing and Shipping," all of which are hereby incorporated herein by reference in their entireties.

FIGS. 1A-1D depict an overview of the system 8 in use. In these implementations, the cartridge 10 is constructed so as to be capable of coupling to, or being provided with, a fluid collection device 1, such as a blood collection device 1 (like those disclosed in co-pending U.S. application Ser. Nos. 13/949,108, 13/750,526, 14/816,994, 14/932,485 or 15/387,177). As shown in FIG. 1C, in various implementations, the fluid collection device 1 comprises an outflow device comprising an outflow channel 49 configured to shuttle fluid from the device 1 into the cartridge 10. In various implementations, this coupling is achieved via a collar (shown at 6) disposed on a connector 18, or other press-fitting techniques, such that it is possible to detach the cartridge 10 from the fluid collection device after filling, as is shown in FIG. 1C. It is further understood that while in fluidic communication with the collection device 1, fluid can exit the device via an outflow channel 49 disposed within an outflow tube 47. Further discussion of this transfer is found below in relation to FIGS. 6A-6C.

Continuing with the use of the system 8 shown in FIGS. 1B-1D, the coupled fluid collection device 1 cartridge 10 unit (generally at 8) is placed on a patient 2 for collection so as to collect fluid onto a substrate 16 or substrates disposed within the cartridge 10. After removal, according to various implementations, it is possible to package the fluid-containing cartridge 10 for storage, transportation and analysis 7, as is shown in FIG. 1D. In various implementations, the substrates 16 are collection or assay substrates 16 disposed within the cartridge 10, and can be comprised of paper, fibrous matrices, or other porous material for the collection and drying of fixed quantities or aliquots of fluid, such as blood or other bodily fluid.

By way of example, where the fluid is blood, the cartridge 10 can be easily inserted into clinical and laboratory equipment or workflows for diagnostics and/or biomarker detections. The various embodiments disclosed or contemplated herein relate to a cartridge 10 device that can be used by untrained or minimally-trained persons to both collect bodily fluid and seamlessly contain the bodily fluid, and related systems and methods.

Figure 2B:
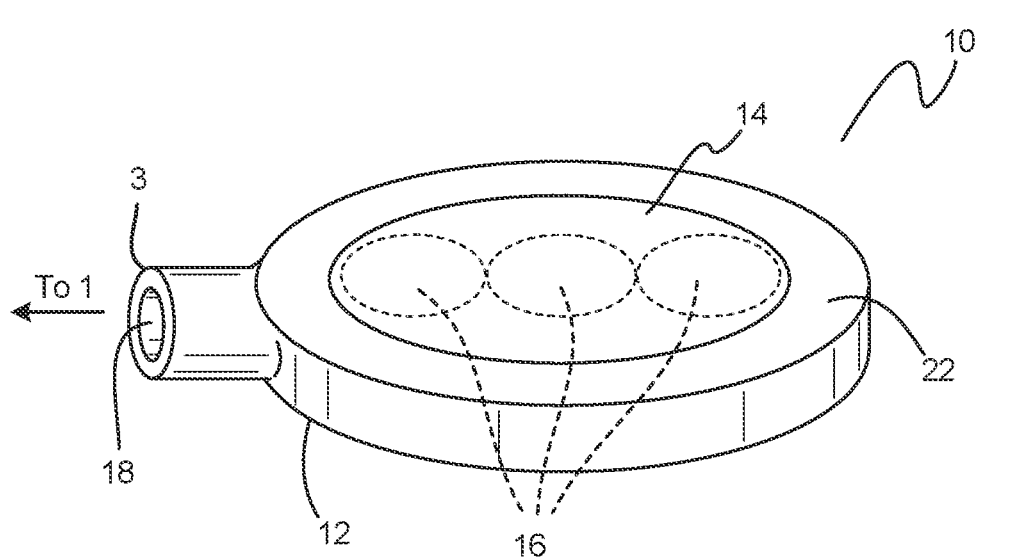
FIG. 2B is a perspective view of the implementation of FIG. 2A with the cover removed.

Various implementations feature a cartridge 10 containing one or more substrate(s) 16 therein for the collection and transport of collected fluid are shown in the implementations of FIGS. 2A-2B. In these implementations, the cartridge 10 has a housing 12 with a central lumen 14 defined within the housing 12. In various implementations, at least one substrate 16 is disposed within the lumen 14, and a coupling 18 or connector 18 is disposed at one end of the housing 12 that is constructed to be physically coupled to the fluid collection device for the intake of fluid into the cartridge 10.

Continuing with FIGS. 2A and 2B, in these implementations the cartridge 10 has a cover 20, such as a removable adhesive cover 20 disposed on one side 22, such as a top side 22, so as to provide for the sealing of the lumen 14 and subsequent removal of stored substrate(s) 16. That is, in certain implementations, the cover 20 is a removable cover 20 that can be affixed to the side 22 by adhesive 24 so as to be capable of being removed when it is desirable to remove the substrate(s) 16.

It is therefore understood that in certain implementations, the removable cover 20 can be removed—such as by "peeling," as shown by reference arrow A in FIG. 2A—to open the lumen 14 and expose the substrate 16, as is shown in FIG. 1B. The collector has thus 2 states; a closed airtight state, and an open state in which the paper or fibrous matrix contained within can be retrieved or dried. It is understood that various other removable cover 20 implementations are possible. In certain circumstances, to avoid unwanted tampering and/or contamination, it is preferable that once the removable cover 20 is removed it cannot be easily replaced.

Figure 2C:
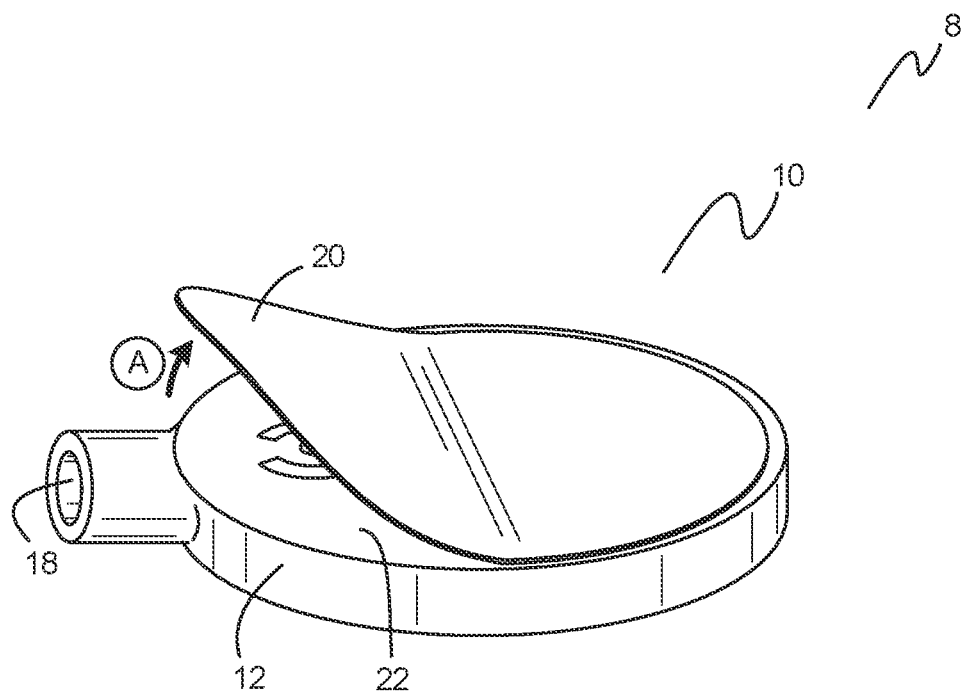
FIG. 2C is a perspective view of another embodiment of the cartridge having apertures disposed on the upper side and containing paper matrices and an adhesive cover that can be removed to access the paper contained within, according to one embodiment.
Figure 2D:
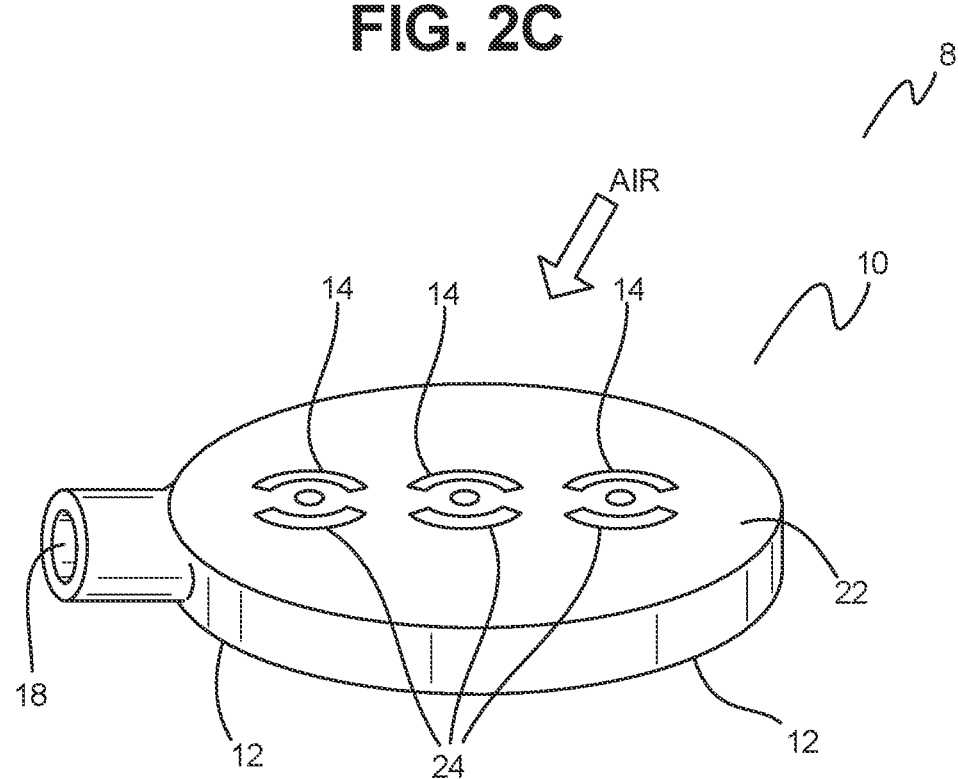
FIG. 2D is a perspective view of the implementation of FIG. 2C with the cover removed.

As best shown in FIGS. 2C and 2D, in certain implementations apertures or vents 24 can be disposed on the cartridge 10, for example on the top side 22 under the cover 20. As shown in FIG. 1C, when the cover 20 is removed in these implementations, as shown by reference arrow A, the vents 24 are exposed (shown in FIG. 2B), allowing the flow of air into the lumen 14 to come into contact with the substrate (not shown). It is understood that in various implementations, vents 24 can prevent contamination and/or tampering with the aliquots and substrate, as the vents can be sized to be smaller than a finger or other possible source of contamination. Further, in certain implementations, it is possible to package the open container with desiccant even before it is air dried and proceed to shipping directly, such that the substrate 16 dries in transit, as is discussed further in relation to FIG. 3D.

In certain implementations, the cartridge 10 can be used to dry and transport the saturated substrates 16 with a variety of approaches. In the implementations of FIGS. 3A-3E, a cartridge 10 having first 22 and second 32 sides is provided. In this implementation, the first side 22 has an opening 22A, and vents 24 are disposed on the second side 32. Both sides 22, 32 can be sealed with covers 20. It is understood that in these implementations, the vents 24 and covers 20 can prevent tampering and/or contamination of the sample, such as in at home use and during the transportation to a lab or other facility for analysis. In these implementations, the vents 24 have several side openings 24A and a central opening 24B. It is understood that alternate vent 24 configurations are of course possible.

Figure 3A:
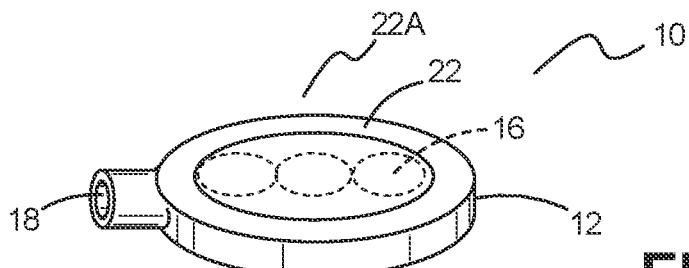
FIG. 3A is a perspective view of another embodiment of the cartridge.
Figure 3B:
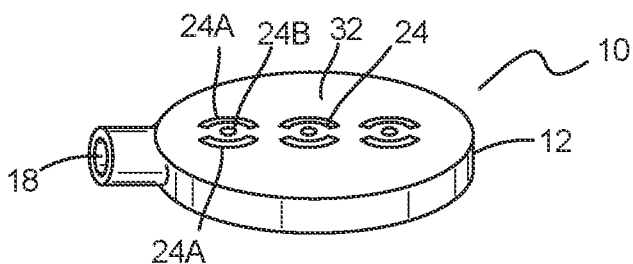
FIG. 3B is a perspective view of an alternate embodiment of the cartridge having apertures disposed on the upper side.
Figure 3C:
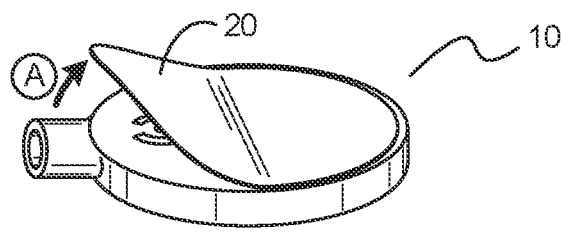
FIG. 3C is a perspective view of an implementation of the cartridge having an adhesive cover over the apertures.
Figure 3D:
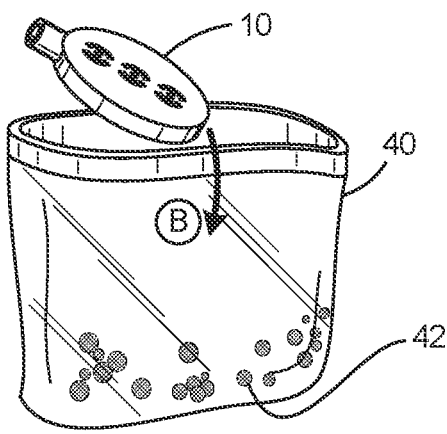
FIG. 3D is a perspective schematic showing the insertion of a cartridge into a pouch or other container.
Figure 3E:
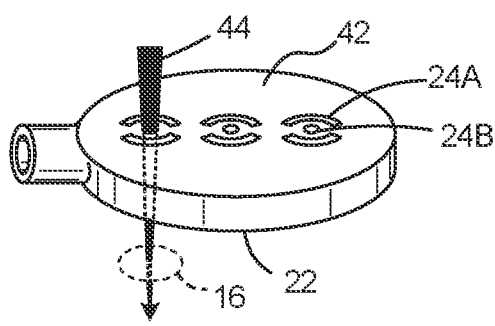
FIG. 3E is a perspective view of a cartridge having apertures that is configured to enable "punch out" removal of the substrates contained therein.

In use, and as shown in the implementations of FIGS. 3C through 3E, the cover 20 is removed after collection (shown at reference arrow A in FIG. 3C). As shown in FIG. 3D, the cartridge 10 is then placed in a sealed container 40, such as a pouch 40, as is illustrated by reference arrow B. In these implementations, the pouch 40 has a desiccant 42. The desiccant 42 of these implementations is able to dry the substrate and sample during storage and transportation without contacting the fluid contained in the substrate.

As is shown in the implementation of FIG. 3E, the substrate 16 can be removed from the cartridge 10 by inserting a rod 44 or other probe through the central vent opening 24B, thereby urging the substrate 16 out the first side 22 opening 22A, as is shown by reference arrow C. It is understood that in certain implementations, the first side opening 22 can be removed prior to removal, while in alternate implementations, the substrate 16 can be urged through the cover.

As would be appreciated, avoiding unnecessary contact between the substrate 16 and surfaces within the lumen 14 provides several advantages. Accordingly, in various implementations of the cartridge 10, the substrate(s) 16 can be suspended within the lumen 14 suspending the substrate 16 means that there are no unwanted channels or concave angles (also called "wedges") adjacent to the substrate 16 where the liquid could be trapped or be diverted. Further, in certain of these implementations the substrate 16 can be highly hydrophilic—such as a paper matrix—thereby enabling or driving capillary flow into the substrate 16, while other aspects of the cartridge 10 and/or lumen 14 can be hydrophobic to prevent the accumulation of fluid or blood in unwanted areas.

The implementations of FIGS. 4A-5I depict several implementations of the cartridge 10 having suspended substrate(s) 16, though alternate implementations are of course possible. As described herein, these implementations can suspend the substrate 16 or substrates with minimal material covering either side of the substrate, yielding certain advantages. Several of these implementations are described herein, but as would be understood, further variations and implementations are contemplated for suspending the substrates within the lumen 14 with minimal contact.

Figures 1, 4A:
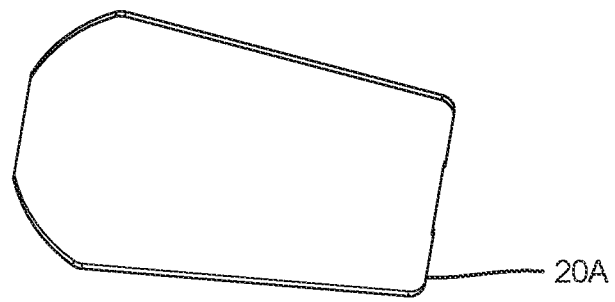
FIGS. 4A-1 through 4A-4 are exploded views of a cartridge having removable upper and lower covers, according to one embodiment.
Figures 2, 4A:
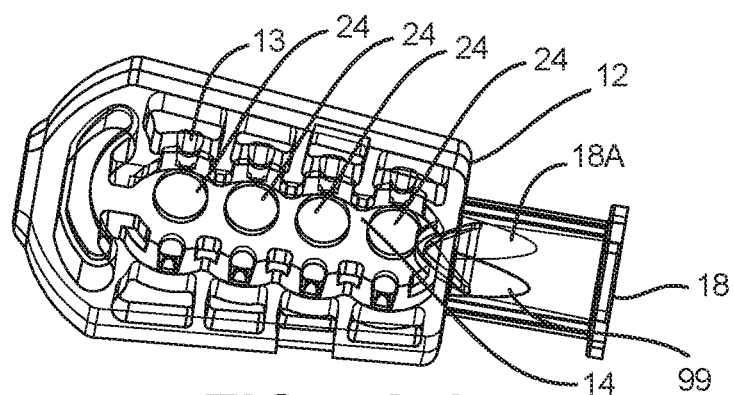
Figures 3, 4A:
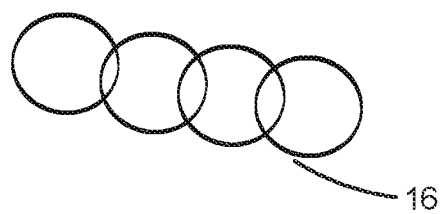
Figures 4, 4A:
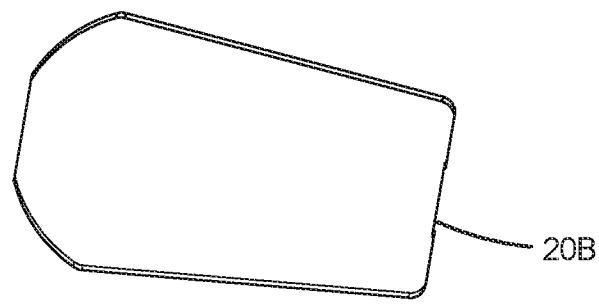

As shown in FIGS. 4A-1 to 4A-4, in certain implementations the cartridge 10 can be assembled with a bottom adhesive cover 20A, substrates 16, and a top adhesive cover 20B. In these implementations, the cartridge 10 has a housing 12 with a central lumen 14, connector 18 and several vents 24, as has been previously described. In these implementations, the substrates 16 are disposed within the lumen via "clips" made up of tabs 54, 56. In various implementations, substrates 16 are disposed within the lumen 14 and secured in place via tabs or projections (as described below in relation to FIGS. 4B-1 through 5I), the housing 12 is able to be covered with the covers 20A, 20B to create a sealed chamber for the substrates 16.

Figure 6A:
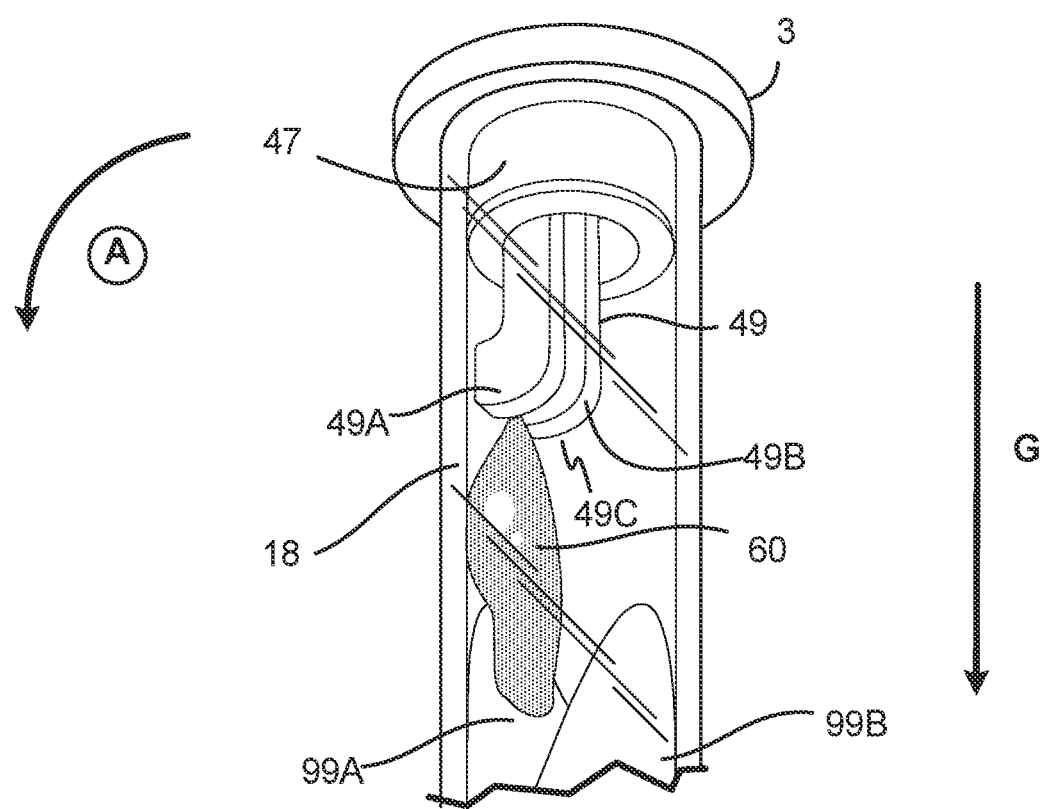
FIG. 6A is a close-up perspective view of the junction and fluidic communication between the connector and a fluid collection device, according to one embodiment.
Figure 6B:
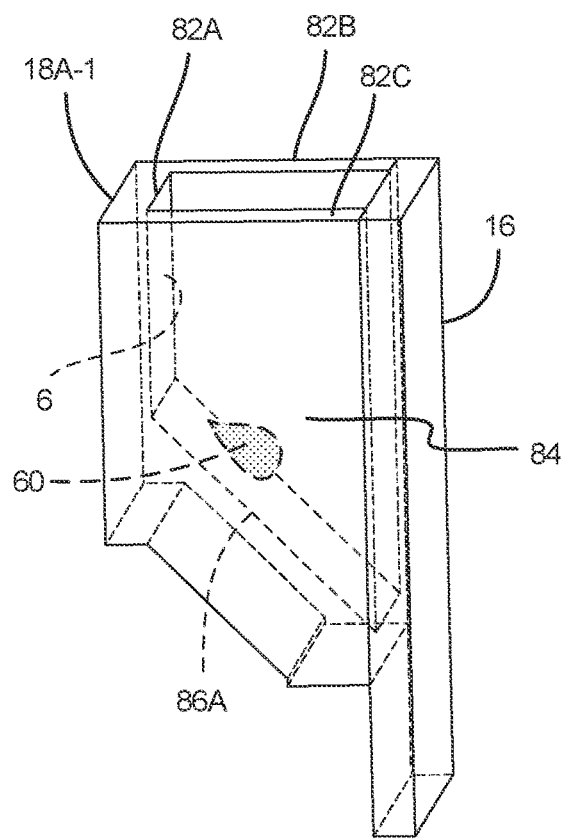
FIG. 6B is a perspective view of an inlet, according to one embodiment.
Figure 6C:
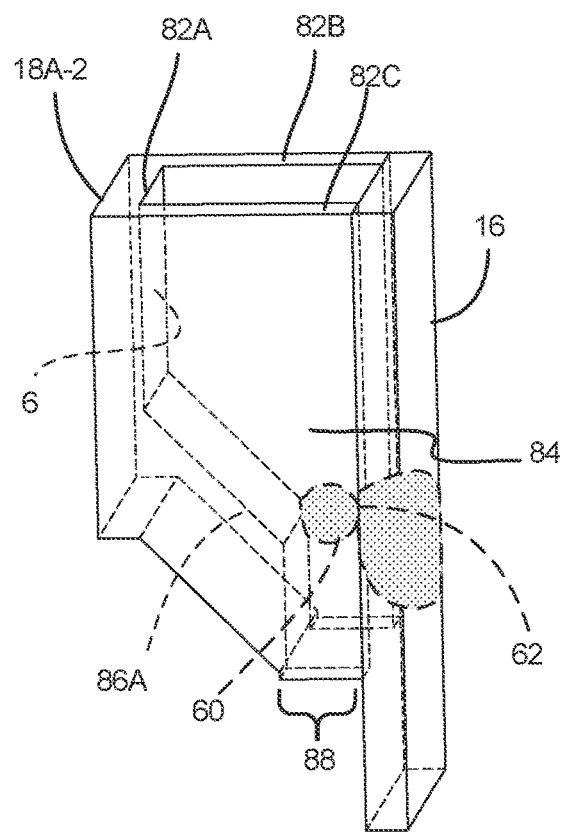
FIG. 6C is a perspective view of an inlet, according to another embodiment.

As shown in FIG. 4A-2, an inlet 18A is disposed within the connector 18. This inlet 18A is configured to be in fluidic communication with an attached fluid collection device (not shown) via a funnel 99 so as to shuttle fluid into the lumen 14 and saturate the substrate 16, as is shown in FIGS. 6A-6C. In various implementations, the inlet 18A comprises a channel, such as an open microfluidic channel, as is discussed below, for example in relation to FIGS. 10A-10B. In various implementations, the funnel 99 is in fluidic communication with the inlet 18A, and in certain implementations the Spontaneous Capillary Flow (SCF) relationship is used for microfluidic channels within the funnel 99 so as to promote capillary flow into the inlet 18A. In further examples, gravitational or other forces urge the fluid into the inlet and onto the substrate.

As would be appreciated, after fluid has been loaded into substrates 16 via the connector 18 and inlet 18A, the lower adhesive cover 20A can be removed to promote drying of the fluid on the substrates 16. Later, the upper adhesive cover 20B can be removed in order to allow the substrates 16 to be removed from the lumen 14.

In certain embodiments, the housing 12 has interlocking components and is configured to secure the substrate(s) 16 within the cartridge 10 so as to have minimal contact within the lumen 14. These interlocking configurations provide numerous advantages, both in manufacturing and during use.

Figures 1, 4B:
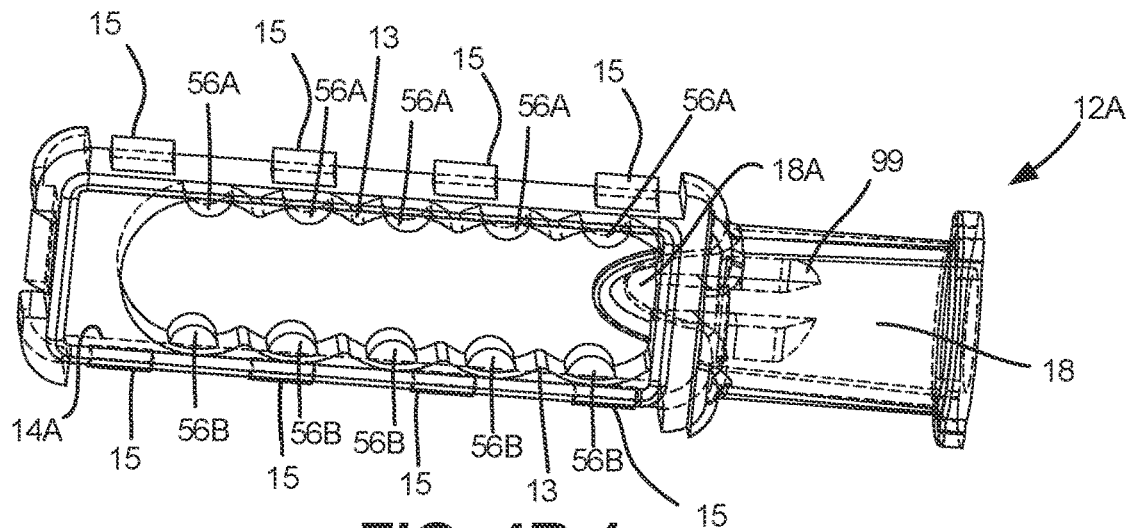
Figures 2, 4B:
Figures 3, 4B:
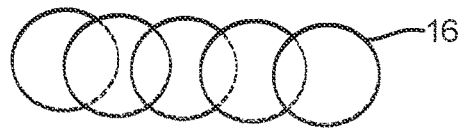
Figures 4, 4B:
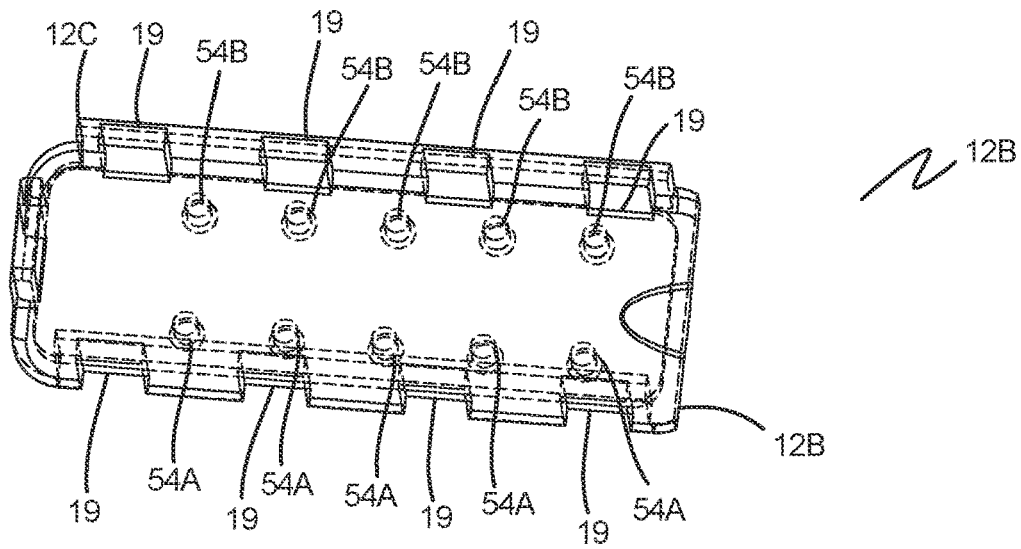

One such interlocking implementation is shown in FIG. 4B-1 to 4B-4, where the substrate 16 is suspended within the housing 12 lumen 14 via an interlocking physical clamp formed by the housing components 12A, 12B. That is, in these implementations, the housing 12 consists of a first portion 12A or lower housing 12A and second portion 12B or upper housing 12B that are configured to engage, interlock or otherwise be fitted together to grasp or secure substrate(s) 16 within the lumen 14 defined by the housing 12.

In these implementations, the lower housing 12B has one or more lower interlocking projections 15 or "catches" 15 disposed along the inner surface 14A of the lumen 14 within the housing 12. Correspondingly, the upper housing 12B comprises one or more paired upper openings 19 or "loops" 19 are disposed within the housing wall 12C and are configured to interlock with the lower projections 15, such that the loops 19 are configured to receive the corresponding opposite projections 15, as would be understood by one of skill in the art. In certain implementations, the upper and lower housings may comprise certain detent features (an example of which is shown in FIGS. 5H-5I at 66) and therefore be interlocked or "snapped" in place to form a unitary housing 12. In alternate implementations, the upper 12B and lower 12B housing portions may be secured to one another via other known methods.

As with certain other examples, in implementations like that of FIG. 4B-1 to 4B-4, the lower housing 12A contains a connector 18 having an inlet 18A, certain implementations of which are described below in reference to FIGS. 6A-6C. Further, in certain of these implementations, the lumen 14 of the lower housing 12A is contoured 13 within to approximate the shape of the substrate(s) 16 disposed therein, as would be appreciated by one of skill in the art.

In the implementation of FIGS. 4B-1 to 4B-4, the substrates 16 are suspended or "clipped" within the lumen 14 between lower supports 56 or tabs and upper supports or tabs 54 when the upper housing 12B is fitted to the lower housing 12A. That is, one or more tabs 56 or "clips" 56 are provided in the lower housing 12A and disposed within the contours 13. It is understood that these components can be formed within the walls of the housing 12 within the lumen, as described herein below.

In use according to these implementations, when the lower housing 12A and upper housing 12B are assembled, the projections 19 are configured to secure over the catches 15, and the gasket 23 creates a substantially water- or air-tight seal between the components so as to suspend the substrates 16 within the sealed lumen 14. That is, the substrates 16 are held in place by the physical clamping forces applied from the bottom clips 56 and top clips 54. After fluid has been loaded into the substrates 16, the loops 19 may be deflected or otherwise released from the catches 15, thereby separating the lower housing 12A from the upper housing 12B and allowing for the removal of the substrates 25.

Figure 5A:
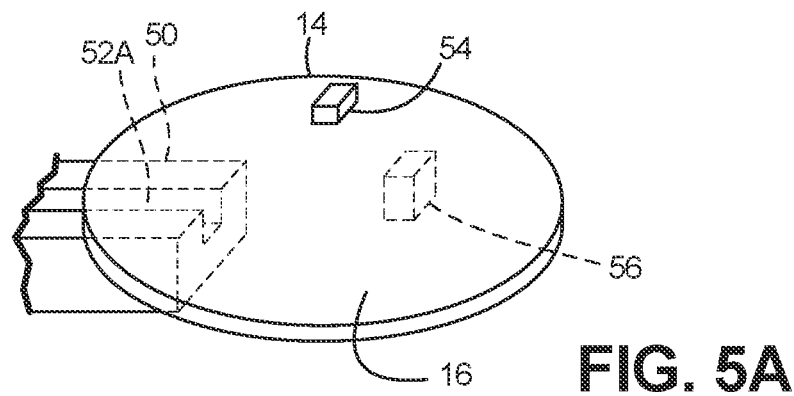
FIG. 5A is a perspective view of the suspension of a substrate within the housing of a cartridge, according to one implementation.

Turning to the implementations of FIGS. 5A, 5B, 5C and 5D, the substrate 16 according to these implementations is disposed and suspended within cartridge 10 in the lumen 14. As shown in FIG. 5A, the substrate 16 can be suspended within the lumen 14 to facilitate reliable transfer of the fluid to the substrate 16, as would be appreciated.

In certain of these implementations, the substrate 16 is disposed within the collector lumen 14 so as to be in fluidic communication with a fluidic channel 50, such as an open channel 50 having a channel opening 52. In various implementations, the open channel 50 can be any of the various channels described in the applications and patents incorporated by reference above, such as those that satisfy the SCF relationship, as has been previously described for example in U.S. application Ser. No. 13/949,108. In these implementations, the substrate 16 is thereby exposed to air on all sides, so as to facilitate accurate volume collection and drying. Further, in various implementations, the substrate 16 need not be in physical contact with the channel 50, so long as the substrate 16 is sufficiently proximal to the channel 50, fluidic bridging can occur, thereby filling the substrate 16.

Figure 5B:
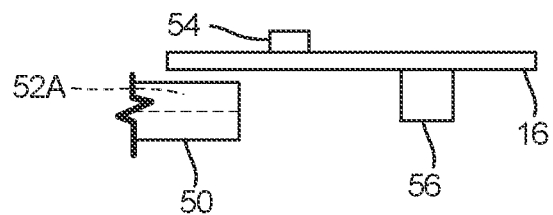
FIG. 5B is a side view of the implementation of FIG. 5A.
Figure 5C:
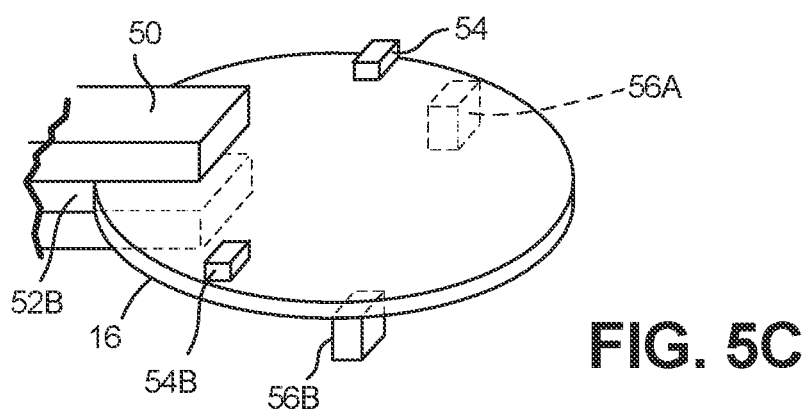
FIG. 5C is a perspective view of the suspension of a substrate within the housing of a cartridge, according to another implementation.
Figure 5D:
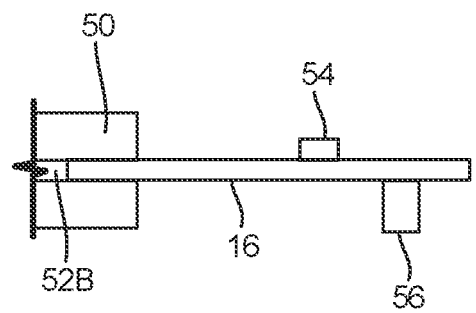
FIG. 5D is a side view of the implementation of FIG. 5C.

In various implementations, the open channel can be a microfluidic channel 50 having a U-shaped channel opening 52A with the substrate 16 disposed adjacent to the open side, as shown in FIGS. 5A and 5B. In alternate implementations, the open channel 50 can be a "sandwich" channel opening 52B shown in FIGS. 5C and 5D, where a portion of the substrate 16 is disposed within the "sandwich." Other implementations are possible, such that fluid is able to pass through the channel opening 52 as has been previously described. For example, in certain implementations, the channel opening 52 can comprise the channel geometry required to facilitate SCF. That is, in various implementations, in these open channels, the ratio of the free perimeter (pf), defined by the length of the cross-section open to air or another medium, and the wetted perimeter (pw), defined by the length of the cross-section made up of solid hydrophilic material must be less than the cosine of the contact angle (θ) of the fluid with the channel walls. When the SCF relation is satisfied, the channel 50 will drive the flow through the microfluidic network by capillary forces. Further demonstration of the use of open channels 50 in various implementations is shown below, in relation to FIGS. 10A-12D.

As shown in FIGS. 5A-5D, in certain alternate implementations the substrate 16 is suspended within the lumen 14 by projections, such as upper tabs 54 and/or lower tabs 56 which are affixed to the housing within the lumen 14. It is understood that many configurations are possible, and that several upper tabs 54A, 54B and/or lower tabs 56A, 56B can be disposed within the lumen 14, such that the substrate 16 can be suspended within the lumen 14. It is understood that in certain implementations, the substrate can "click" into place between the tabs 54, 56, thereby improving the transfer fluid from a channel to the substrate 16. In various implementations, the tensile strength of the substrate can provide sufficient spring force to retain the substrate in a fixed position between the various tabs 54, 56. It is also understood that in certain implementations, a spring (not shown) can be provided to urge the tabs 54, 56 into a clasping position on either face of the substrate 16.

FIGS. 5E-5I show further implementations for securing the substrate 16 within the housing 12 via projections, "clips" or tabs 54, 56 disposed on either side of the lumen 14 and configured to secure the substrate(s) 16.

Figure 5E:
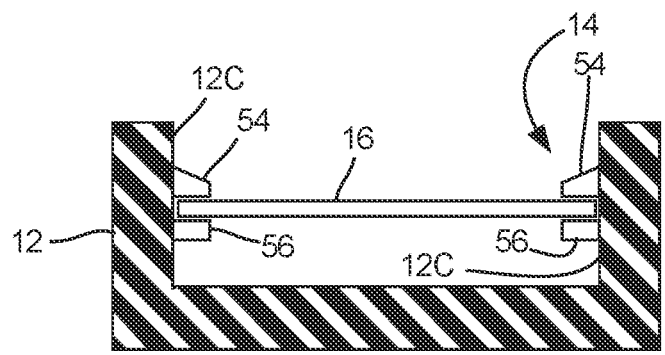
FIG. 5E is a cross-sectional view of a substrate suspended within the housing according to one implementation.

In the implementation FIG. 5E, a single primary housing 12 contains bottom tabs 56A, 56B and top tabs 54A, 54B that are fixedly attached to the sides 12C of the housing 12 within the lumen 14. A substrate 16 may be introduced from above such that it is suspended between the bottom tabs 56 and top tabs 54.

Figure 5F:
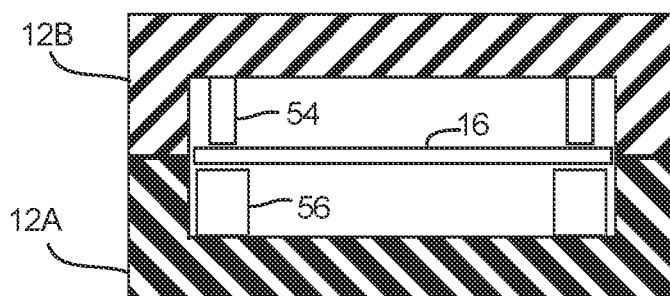
FIG. 5F is a cross-sectional view of a substrate suspended within the housing according to another implementation.

As shown in FIG. 5F, a lower housing 12A containing bottom tabs 56A, 56B configured to interface with a upper housing 12B having top tabs 54A, 54B so as to secure the substrate 16 therein. It is understood that in these implementations, the substrate 16 can be introduced between the bottom tabs 56A, 56B and top tabs 54A, 54B, such that when the lower housing 12A and upper housing 12B are interfaced together, the substrate 16 is held in place due to the clamping force between the bottom tabs 56A, 56B and top tabs 54A, 54B.

Figure 5G:
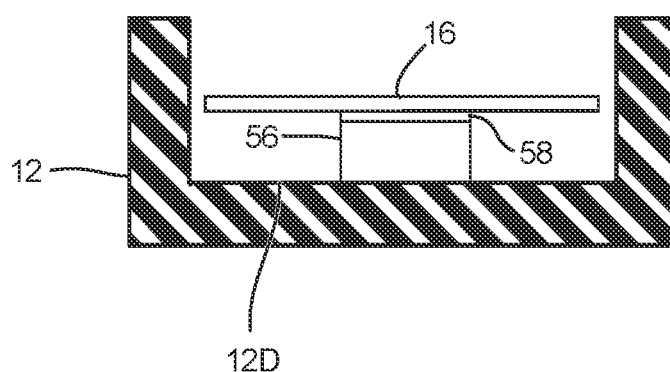
FIG. 5G is a cross-sectional view of a substrate suspended within the housing according to yet another implementation.
Figure 5H:
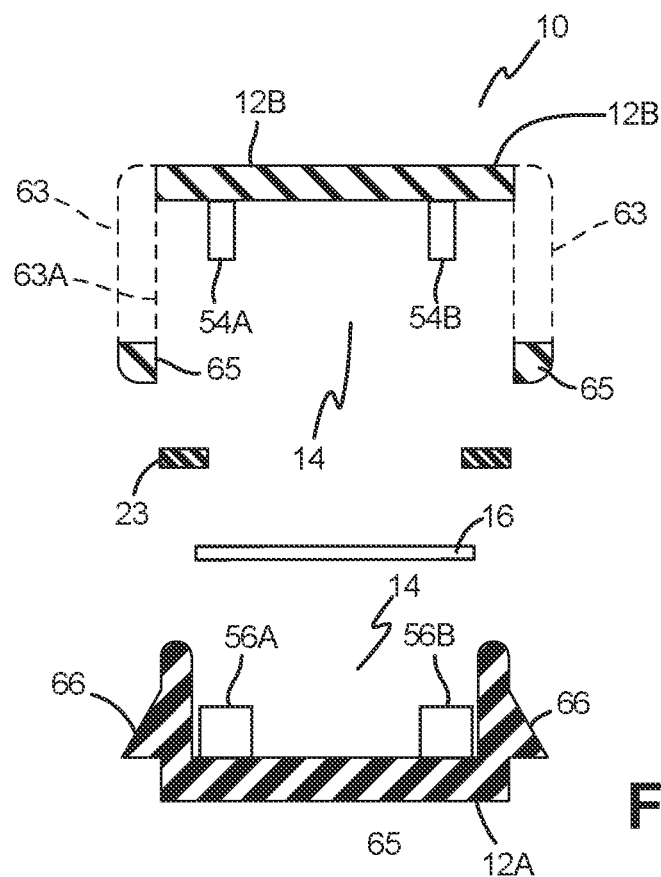
FIG. 5H is an exploded cross-sectional view of one implementation of an interlocking housing securing a substrate therein.
Figure 5I:
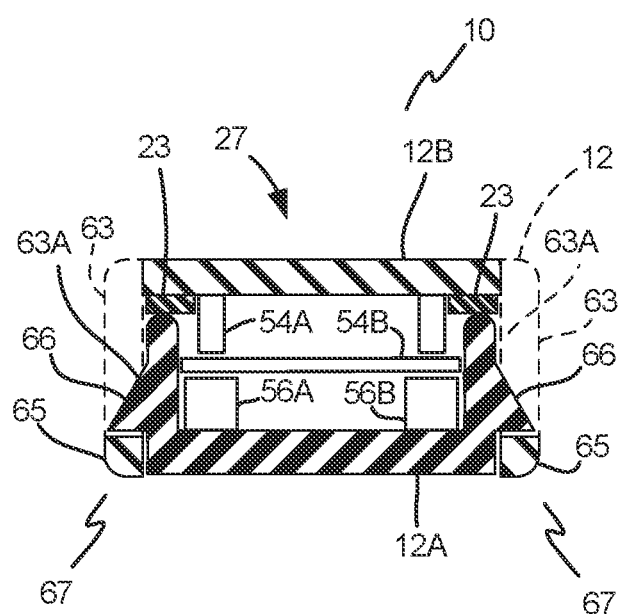
FIG. 5I is a cross-sectional view of the housing implementation of FIG. 5I with the housing portions interlocked.

As shown in FIG. 5G, substrate 16 may be adhered to a single primary housing 12 via a single tab 56 projected from the top or bottom 12D of the housing 12 by way of adhesive 58. In various implementations, the adhesive 58 can be a double-side tape with plastic backing, a transfer tape without a plastic backing, or a liquid adhesive.

FIGS. 5H-5I show cross-sectional side views of a device 10 assembly consisting of a lower housing 12A and an upper housing 12B. In these implementations, the lower housing 12A contains bottom tabs 56A, 56B disposed within the lumen 14, and features detent features or protrusions 66 disposed along on either side along the outer surface of the housing 12. It is understood that these protrusions 66 enable the upper 12B and lower 12A portions of the housing to be snapped together.

In turn, the upper housing 12B of FIGS. 5H-5I has paired top tabs 54A, 54B disposed with the lumen 14. The housing 12B further has sides 63 having openings 63A therein and stops 65, wherein the upper housing 12B is thereby adapted to be capable of being snapped into place over the lower housing so as to prevent the removal of the upper housing 12B from the lower housing 12A, as would be readily appreciated. As described herein, this catch mechanism (generally at 67) can thereby be used to secure the housing 12 together.

In these implementations, a gasket 23 is also provided, as described above, such that in use when the lower housing 12A is pressed together with the upper housing 12B, the stops 65 temporarily deflect and then secure around the protrusions 66 to form the catch mechanism 67. Accordingly, the gasket 23 compresses against the lower housing 12A and the upper housing 12B, creating an air- or water-tight seal, such that the substrate 16 is fixedly suspended within the lumen 14 for use.

Further embodiments of the fluid collection device outflow channel 49 and corresponding inlet 18A implementations are contemplated in FIG. 6A and FIGS. 6B-C. In certain implementations the coupling is achieved by way of a fitting on the connector 18, which is also a "collar" 3. In various implementations, the collar 3 can be pressure fit and include a rubber gasket, a thread, or a quarter turn lock. It is understood that in various implementations, the connector 18 is therefore configured to couple directly with a fluid collection device 1 to create a fluidic and/or hermetic seal and facilitate the flow of fluid via the connector 18 into the cartridge 10. The connector 18 of various implementations can contain an inlet (shown for example in FIGS. 4A-2 and 4B-1 at 18A and in FIGS. 6B-6C) that is in fluidic communication or otherwise integrated with a funnel 99 disposed within the connector 18 that is configured to receive and shuttle fluid from the device 1 to the lumen 14 via the connector 18. It is understood that in various implementations, the funnel 99 and inlet 18A may be the same component.

In certain embodiments, an outflow channel 49 can extend from an outflow tube 47 from the fluid collection device (as shown in relation to FIG. 1C). In these embodiments, the outflow channel 49 extends from the outflow tube 47 such that the distal end of the channel 49C is disposed within the connector 18, thereby providing the initial transitional point for the flow of fluid 60 into the cartridge 10. It is understood that these outflow channels 49 contemplate outflow channel geometries that act as one-way flow valves. In this sense, the fluid 5 is able to flow by dripping into the cartridge 10, but when the device 1 and cartridge 10 are inverted, the channel 49 will not allow backflow out of the tube. Many of these geometries are described in the incorporated reference U.S. application Ser. No. 14/816,994.

The implementation of FIG. 6A features an outflow channel 49 having first 49A and second 49B channel edges which are in fluidic connection with the inner surface 6 of the connector 18 and/or the inlet 18A. That is, the two channel edges 49A, 49B are in contact with the inner surface 6 of the inlet 18A such that fluid 60 that flows out of the outflow channel 49 will come in contact with the inner surface 6 of the inlet lumen 84. Thus, when the device and connector 18 are substantially upright, the fluid is able to flow out from the outflow channel 49 and into the inlet 18A, and when it is rotated in the direction of reference arrow A fluid 60 is brought into contact with the inner surface 6 so as to fill the inlet reservoir, discussed in relation to FIGS. 6B-C. It is understood that many other configurations are contemplated, as have been previously discussed.

FIGS. 6B-6C show two implementations for inlet 18A designs for the application of fluid onto substrates 16, as was shown in FIG. 4A-4B. In these implementations, the inlet 18A is in fluidic communication with the connector so as to accept the flow of fluid into the housing. The inlets 18A-1, 18A-2 of these implementations have several sides 82A, 82B, 82C abutting against a substrate 16 and defining an inlet lumen 84. In these implementations, a distal plane 86A is provided at the end of the lumen 84 proximal the interior of the housing.

As shown in FIG. 6B, in one implementation of the inlet 18A-1 fluid 60 makes contact with a substrate 16 at a vertical wall (shown here at 82A within the lumen 84). Thus, any fluid that enters the inlet 18A-1 may only exit through the substrate 16 and components of the fluid may be filtered as the fluid flows down the length of substrate 16.

As shown in FIG. 6C, an alternate implementation of the inlet 18A-2 may instead have a gap 100 separating it from a substrate 16. Thus, fluid may exit the inlet 18A-2 by flowing through the substrate 16 or by flowing through the gap 88. It is understood that typically, fluid flows more quickly out of the inlet 18A-2 of FIG. 6B than the inlet 18A-1 of FIG. 6A, due to the presence of the gap 88, with specific flow rate dependent on the size of gap 88 and the hydrophilicity of the inlet 18A-2, as would be appreciated by a skilled artisan.

That is, when the width 88 of the gap 88 is less than approximately 100 μm, the flow of fluid through gap 88 is minimal due to the effects of surface tension. When the width 88 is greater than approximately 200 μm and less than approximately 400 μm, the majority of the fluid flows out of inlet 18A-2 through the gap 88 along the entire width of substrate 16, as sufficient fluid must accumulate at gap 88 before the fluid has sufficient hydrostatic pressure to overcome the effects of surface tension. The fluid reaches distal regions of substrate 16 by first flowing down the outer surface of substrate 16 and then transporting within its fibers. Overall, the rate of filling of substrate 16 is increased when using inlets 18A-2 like those of FIG. 6B as opposed to inlets 18A-1 without a gap 88, as depicted in FIG. 6A, and less filtering of fluid components within the substrate 16.

By way of example, in certain implementations the filtering of red blood cells from whole blood occurs. It is further understood that when the distance of the gap 100 is greater than approximately 500 μm, the fluid is able to flow out of the inlet 18A-2 with minimal accumulation along the gap 100. Thus, fluid is able to flow down the side or edge of the substrate 16 without covering its entire width, which can result in incomplete filling of substrate 16. While the widths 100A discussed above are relevant when the fluid used is whole blood and the width of the substrate is approximately 8 mm, the gap 88 distances used may vary in alternate implementations based on factors such as fluid viscosity, material surface properties, surface treatments, and the specific geometries of the inlet and the substrate.

Figure 7A:
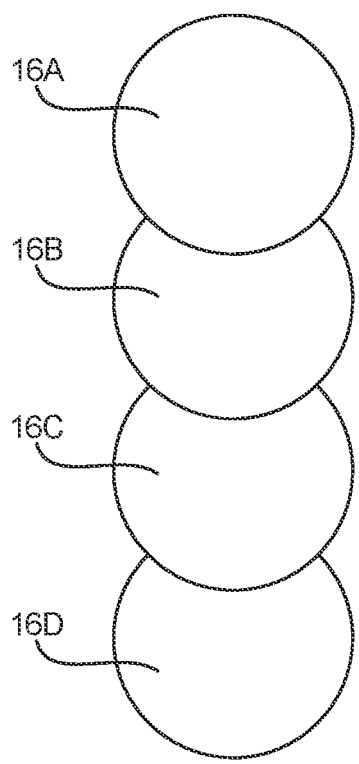
FIG. 7A is a top view of one embodiment of overlapping, adjacent substrates.
Figure 7B:
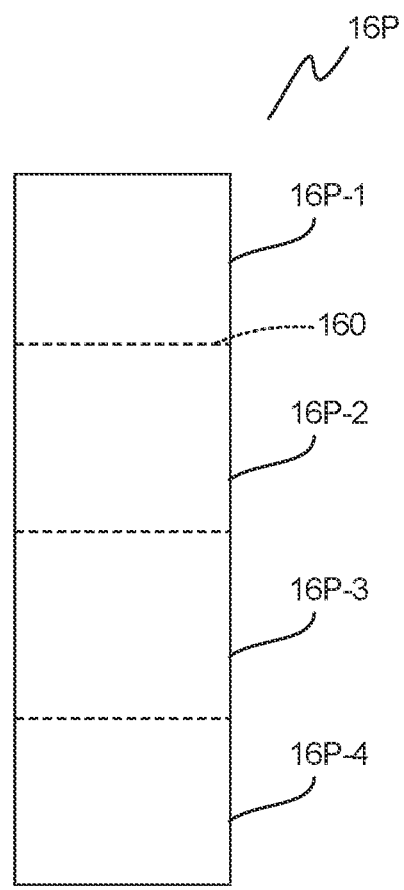
FIG. 7B is a top view of an alternate embodiment of a substrate having several subunits.

As shown in FIGS. 7A-B, in varying implementations, substrates 16 may consist of multiple discrete substrates 16A, 16B, 16C, 16D or a single continuous perforated strip 16P comprising several subunits 16P-1, 16P-2, 16P-3, 16P-4.

In FIG. 7A, multiple round substrates 16A, 16B, 16C, 16D are arranged such that they are partially overlapping. It is understood that fluid is able to flow from one substrate to the next through regions of overlap. Substrates of alternate geometries such as ellipses or rectangles may also be used in place of round substrates.

As shown in FIG. 7B, a single continuous substrate 16P may be separated into subunits 16P-1, 16P-2, 16P-3, 16P-4 by perforations 160. The perforations 160 retain fluidic continuity during fluid collection, while allowing the substrate 16 to be broken apart into individual segments 16P-1, 16P-2, 16P-3, 16P following fluid collection. The perforated substrate 16P need not be limited only to a rectangular geometry with rectangular components. For example, a single substrate 16P made out of smaller perforated circular or ellipsoid segments may also be used.

Figure 8A:
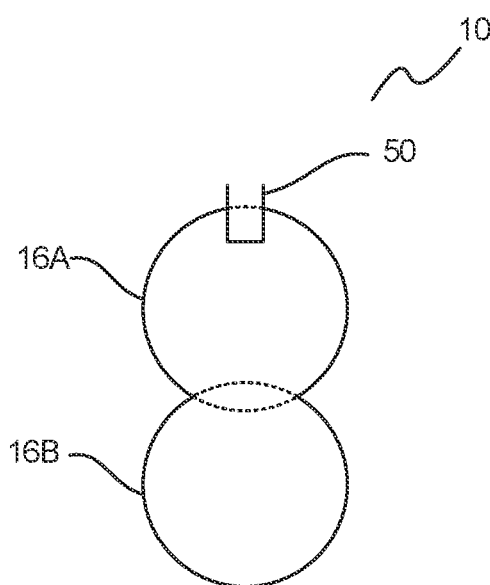
FIG. 8A is top view of adjacent substrates in fluidic communication with a microfluidic channel.
Figure 8B:
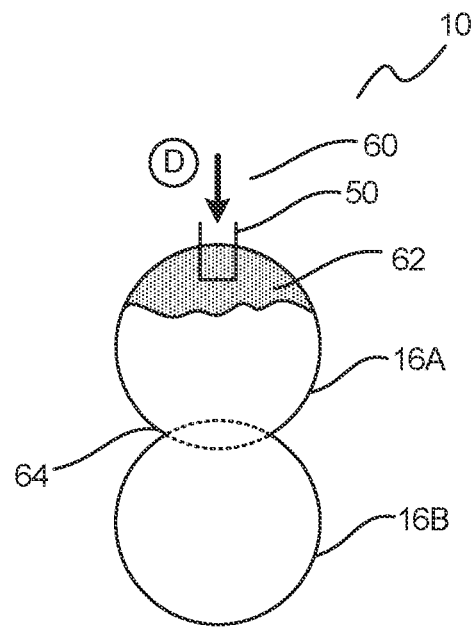
FIG. 8B is a top view of the implementation of FIG. 8A, showing partial substrate saturation.
Figure 8C:
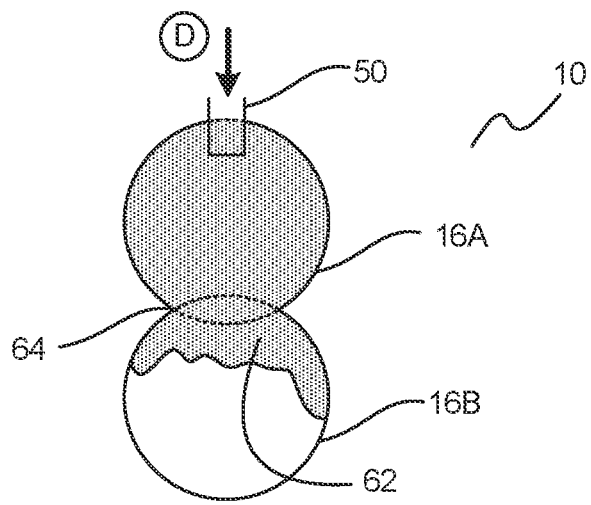
FIG. 8C is a top view of the implementation of FIG. 8A, showing further substrate saturation, including the saturation of a second adjacent substrate.

Turning to FIGS. 8A, 8B and 8C, certain implementations of the cartridge 10 facilitate the controlled, sequential filling of several substrates 16A, 16B. In these implementations, fluid 60 passing through the channel 50 (shown by reference arrow D) is able to come into contact with a first substrate 16A (shown in FIG. 8A), flow into (FIG. 8B) and eventually saturate 62 the substrate 16A.

As shown in FIG. 8C, in these implementations, a second substrate 16B disposed adjacent to the first 16A but opposite the channel 50 will begin filling after the first 16A has become saturated such that the fluid has reach the intersection 64 between the substrates 16A, 16B. It is understood that the intersection 64 between the substrates 16A, 16B need not involve direct physical contact between the substrates 16A, 16B: the substrates 16A, 16B merely need to be disposed sufficiently proximally to allow for fluidic bridging between the first 16A and second 16B substrates. Further discussion of various implementations is found below, for example in relation to FIGS. 16A-C.

Figure 9:
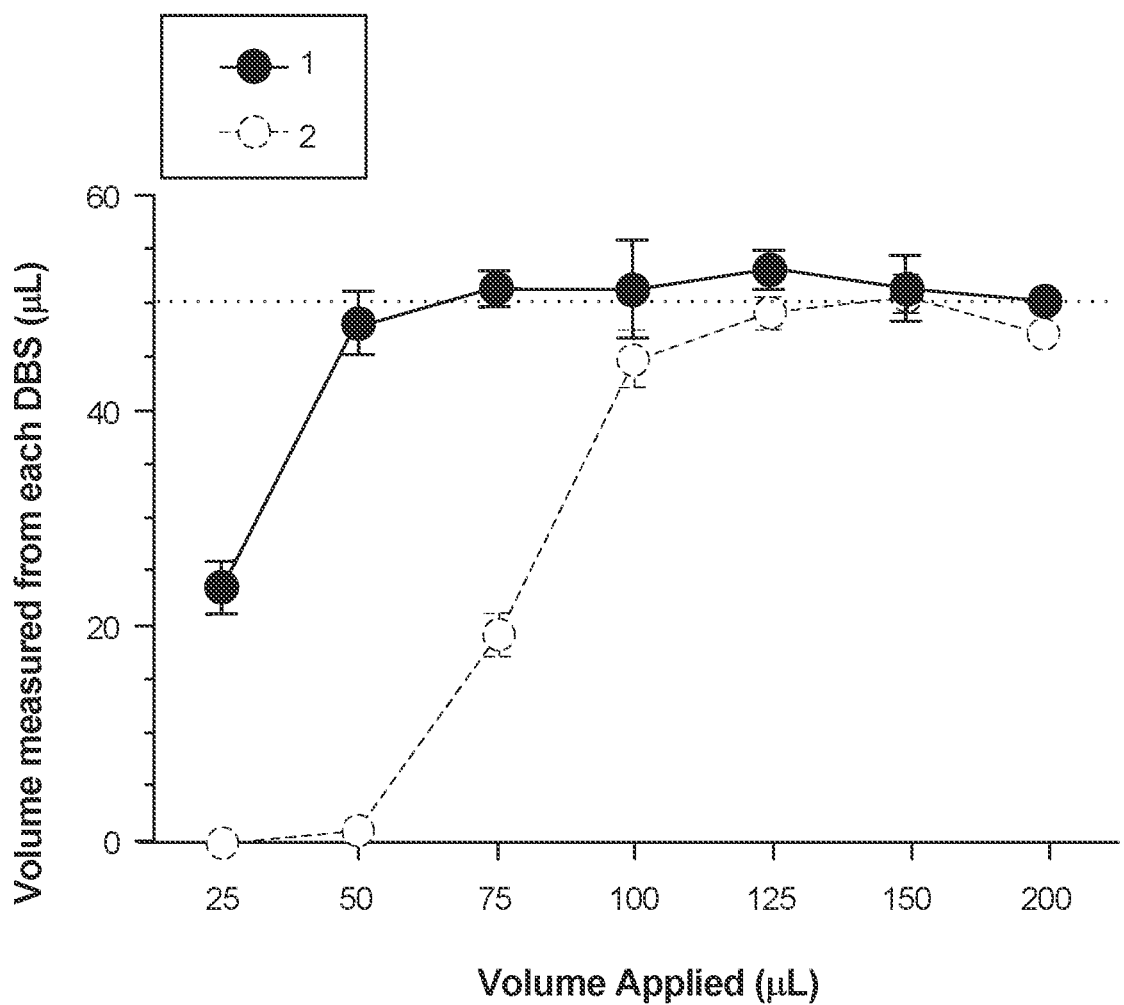
FIG. 9 is a graph showing the volume control ability of a cartridge containing multiple paper substrate(s) in which variable blood volumes are inputted.

This sequential saturation of the substrates 16A, 16B is demonstrated in FIG. 9. In FIG. 9, controlled volumes of fluid were introduced into a collector having first (black circles) and second (white circles) substrates configured to be saturated at 50 μL were disposed substantially as shown in FIGS. 8A-8C. As is shown in FIG. 9, the second substrate (white circles) does not begin to fill until the first has reached the saturation point of approximately 50 μL. After 100 μL or more has been introduced, the substrates do not retain any additional fluid. Further discussion of excess fluid management is found below, for example in relation to FIGS. 10A and 11A. It is understood that the volumetric capacities of these components are correlated to surface area—in various implementations the capacity can be any size.

Figure 10A:
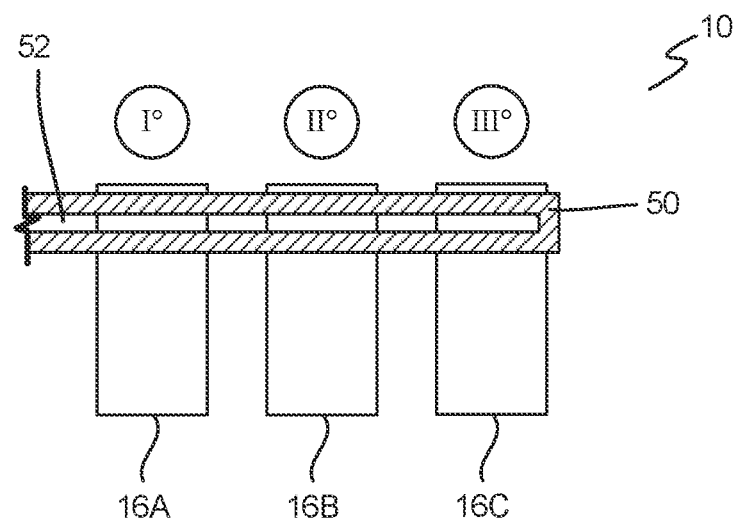
FIG. 10A is a top view of the interior of the cartridge lumen having several spaced substrates connected by a microfluidic channel, according to one embodiment.
Figure 10B:
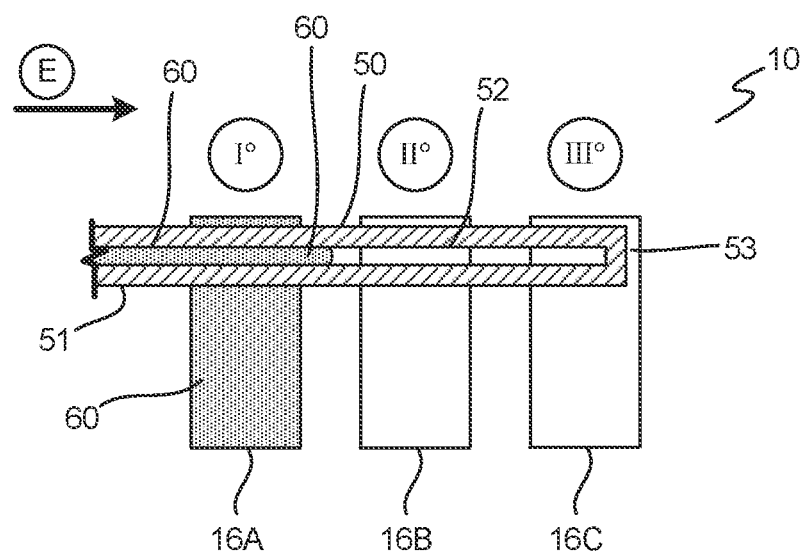
FIG. 10B is a further top view of the implementation of FIG. 10A showing the sequential saturation of the substrates.

In one embodiment, the substrates 16A, 16B, 16C are in fluidic communication with a channel 50, such as an open channel satisfying the SCF relationship, as shown in the implementations of FIGS. 10A-10B. In these implementations, a plurality of substrates 16A, 16B, 16C are provided that are, in this embodiment, substrate(s) 16A, 16B, 16C. It is understood that various other substrates may be utilized, such as paper discs, glass fibers, foams, porous solids and other materials capable of sufficient capillary force to self-fill with liquid that is thus sequestered in the substrate. It is understood that it is important to compare the capillarity of the substrates in certain implementations, as one important factor for controlling volume is that the substrate provides strong capillary force, thus allowing for self-filling so long as it is not in fluidic communication with another substrate with a stronger capillary force. In various implementations, a material of similar capillary force can be adjacent to it and will absorb the overflow.

In the implementations of FIGS. 10A-10B, the substrate(s) 16A, 16B, 16C are disposed within the housing (as shown variously above) so as to be in fluidic communication with and sequentially filled via the channel 50, which in this implementation is an open microfluidic channel 50 having an opening 52. It is understood that various channel 50 shapes and geometries may be utilized, and that certain implementations will result in spontaneous capillary flow along the channel 50, as has been previously described in the incorporated references. It is further understood that in implementations having an opening 52, the substrate(s) 16A, 16B, 16C can be disposed adjacent to the opening 52 to facilitate fluid 60 transfer and/or bridging, as would be apparent to one of skill in the art.

In these implementations and as shown in FIG. 10B, the substrate(s) 16A, 16B, 16C are disposed in a linear orientation inside the housing. In these implementations, preferential saturation facilitates sequential saturation by the open channel 50, as described herein. In these embodiments, a first substrate 16A is disposed adjacent to the proximal channel end 51 and a last substrate 16C is disposed adjacent the distal end 53. The capillarity of the substrate(s) 16A, 16B, 16C in these implementations is greater than the capillarity of the open channel 50, such that fluid 60 flowing into the collector (shown by reference arrow E) sequentially saturates each substrate 16A sequentially (designated by I°, II°, and III°), prior to advancing distally through the channel 50 to subsequent substrate(s) 16B, 16C. It is understood that further numbers of substrates or substrate(s) can be provided.

As shown in FIG. 10B, these implementations therefore allow for the preferential saturation of the proximal substrate 16A prior to saturation of the subsequent substrate(s) 16B, 16C. As is shown in FIG. 10B, sequentially saturation occurs because fluid 60 will preferentially enter the first substrate 16A prior to saturation, at which point it will continue to flow through the channel 50.

In certain implementations, such as in a blood draw, it is possible that excess fluid will enter the collector—meaning more fluid than the saturation capacity of the assay substrate or substrates 16A, 16B. In these implementations, an overflow reservoir 70 can be provided.

Figure 11A:
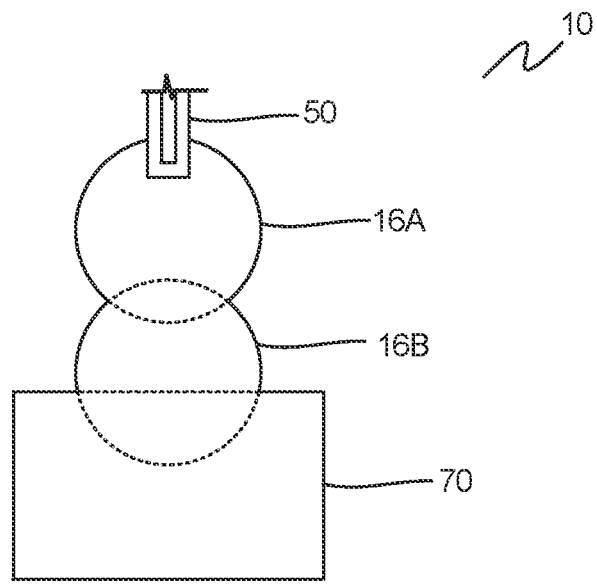
FIG. 11A is a top view of the interior of the cartridge lumen having several adjacent substrates and a reservoir, showing one embodiment for making precise aliquots of fluid onto substrates regardless of the volume inputted by absorbing the overflow onto the reservoir.
Figure 11B:
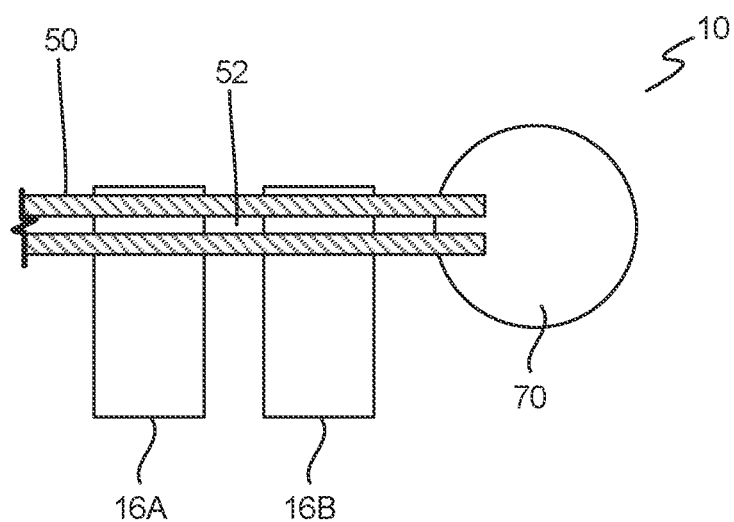
FIG. 11B is a top view of the interior of the cartridge lumen according to a further embodiment having several spaced substrates connected by a microfluidic channel and a reservoir.

In the implementations of FIGS. 11A and 11B, the cartridge 10 has an overflow reservoir 70, such as a sponge or high-absorbance paper 70, though it is understood that various other substances or structures can be used as well. The overflow reservoir 70 is able to collect the additional fluid and prevent pooling within the housing. It is understood that in certain implementations the assay substrates 16A, 16B can have fixed saturation volumes—for example 50 µL, 100 µL or 150 µL—while the overflow reservoir 70 can have a much larger saturation volume. As is shown in the implementation of FIG. 11A, the overflow reservoir can be used in conjunction with adjacent substrate(s) 16A, 16B, such as in the implementations of FIGS. 8A, 8B and 8C, while in FIG. 11B, the overflow reservoir 70 is used in conjunction with an open channel 50 and spaced substrate 16A, 16B configuration, like that of FIGS. 10A and 10B. It would apparent to one of skill in the art that further configurations are possible.

Figure 12A:
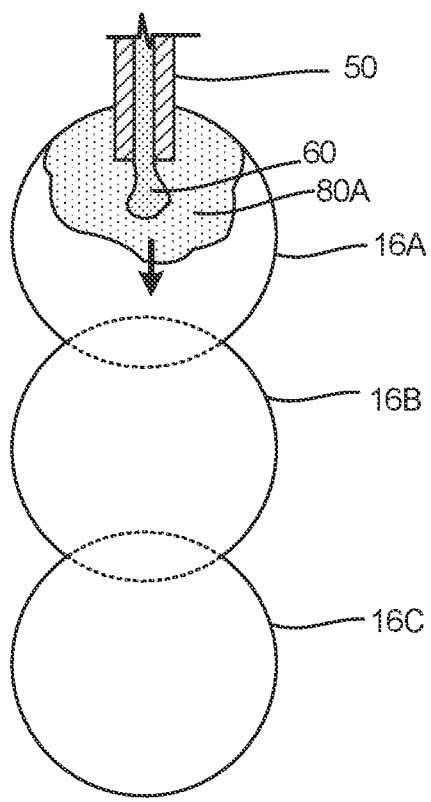
FIG. 12A is a top view of the interior of the cartridge lumen having adjacent substrates containing different compositions and chemical additives for orthogonal clinical readouts, wherein the substrates are connected by a microfluidic channel, according to one embodiment.

As shown in the implementation of FIG. 12A, a substrate 16A can comprise a reagent 80A, such as a blood lysis reagent, a nucleic acid stabilization reagent, a chaperone molecule to protect a specific blood analyte or other known reagents used in the clinical analysis of fluids such as blood or plasma: myriad examples are known. In these implementations, the reagent 80A can be applied to one or more of the substrates 16A prior to use, such that fluid 60 saturating the substrate 16A is exposed to the reagent 80A prior to drying and storage. In the implementation of FIG. 12A, three adjacent substrates 16A, 16B, 16C are shown, but in additional implementations, other configurations are of course possible.

Figure 12B:
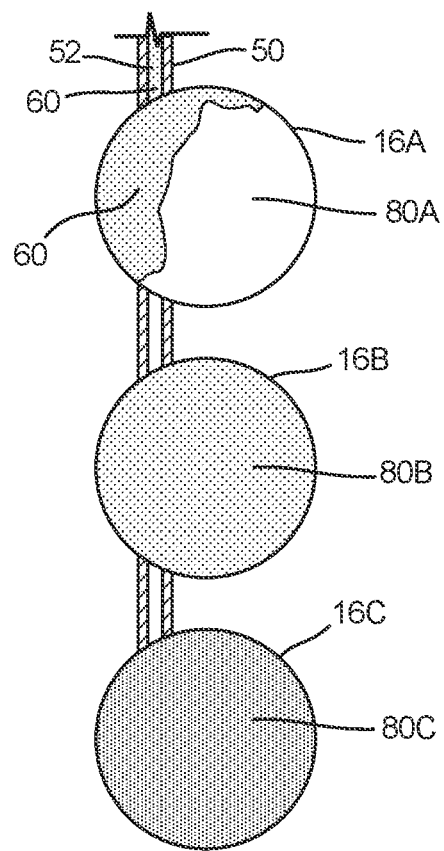
FIG. 12B is a top view of the interior of the cartridge lumen having spaced substrates containing different compositions and chemical additives for orthogonal clinical readouts, wherein the substrates are connected by a microfluidic channel, according to one embodiment.
Figure 12C:
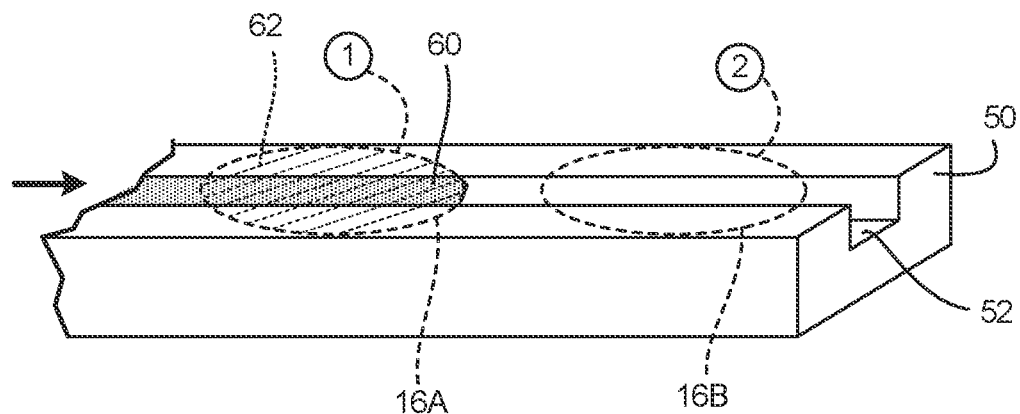
FIG. 12C is a perspective view of several spaced substrates in fluidic communication with an open microfluidic channel, according to one embodiment.
Figure 12D:
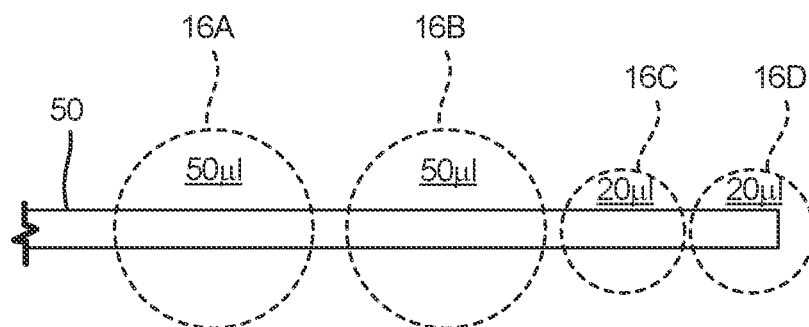
FIG. 12D is a top view of the interior of the cartridge lumen having spaced substrates of varying size, according to one embodiment.

Accordingly, in the implementation of FIG. 12B, the substrates 16A, 16B, 16C are in fluidic communication with an open channel 50. In this implementation, the downstream substrates 16B, 16C have been treated with reagents 80B, 80C. A skilled artisan will appreciate that because of the sequential nature of the substrate saturation, in certain implementations certain reagents can be pre-applied to any or all of the substrates 16A, 16B, 16C. It is understood that in certain circumstances it is beneficial to apply certain reagents 80B, 80C to downstream substrates 16B, 16C so as to prevent cross-contamination, as certain reagent may enter the fluid 60 and be carried down the channel 50 into a downstream substrate. In certain implementations, the sequential filling of the substrates 16A, 16B, 16C via a channel 50 facilitates substrate bypass, meaning the flowing fluid is not drawn toward a saturated substrate 16A, instead passing by the saturated substrate 16A to fill a subsequent substrate 16B, 16C with minor co-mingling or contamination from upstream substrate reagents. The advantages of minimizing co-mingling are apparent.

As shown in the implementations of FIGS. 12C-15D, in various implementations, substrates 16A, 16B, 16C, 16D of various capacities can be distributed along the channel 50 for sequential saturation.

Figure 13A:
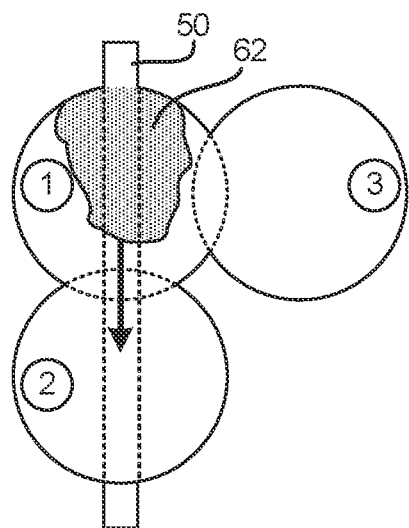
FIG. 13A is a top view of the interior of the cartridge lumen having adjacent substrates and a microfluidic channel.
Figure 13B:
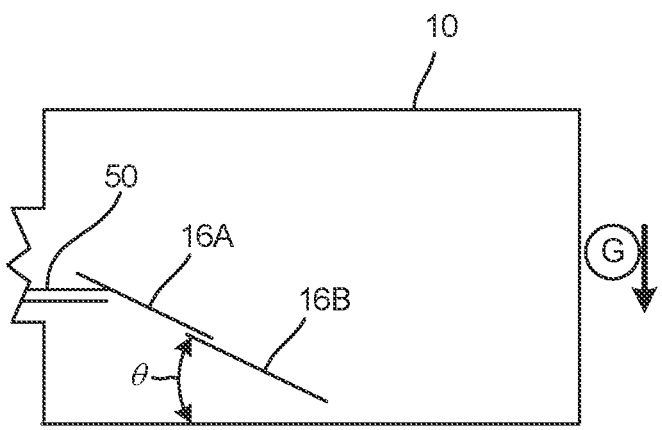
FIG. 13B is a side view of the interior of the cartridge lumen having adjacent substrates and a microfluidic channel, wherein the substrates are disposed so as to utilize gravity for preferential saturation of the substrates.
Figure 13C:
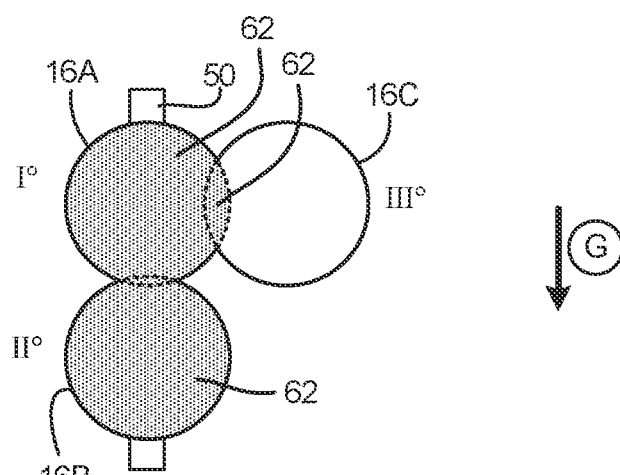
FIG. 13C is a top view of the implementation of FIG. 13B, showing the sequential saturation of the substrates.

As best shown in FIGS. 13A, 13B and 13C certain implementations of the cartridge 10 can use gravity (shown generally with reference arrow G) to control the sequence of substrate 16A, 16B, 16C saturation 62 from the channel 50. As shown in FIGS. 13A-13B, the force of gravity combined with the capillarity of the substrates 16A, 16B, 16C will lead to preferential fluid 60 saturation in a determined sequence, as is generally shown in FIG. 13C.

Figure 14A:
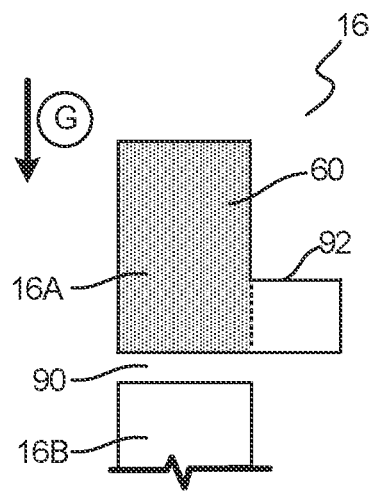
FIG. 14A is a top view of a substrate embodiment having a gap and a shunt.
Figure 14B:
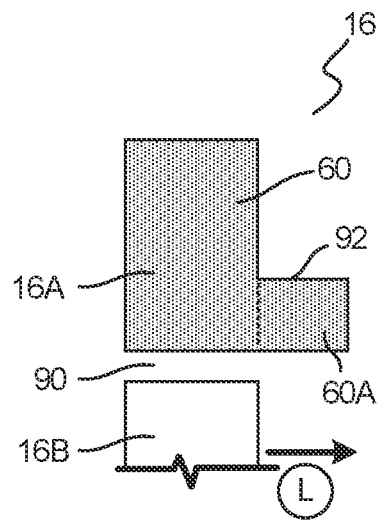
FIG. 14B is a further top view of the implementation of FIG. 14A showing saturation of the shunt.

As best shown in FIGS. 14A-14B, in certain implementations, the substrate 16 can utilize selective fluidic bridging. That is, in certain implementations, a substrate 16 can be provided that has a first substrate portion 16A and a second substrate portion 16B disposed across a gap 90. In certain of these implementations, a shunt 92 is also provided adjacent to, and in direct communication with the first substrate portion 16A. In the implementations of FIGS. 11A-C, the static substrate reservoir 19 is provided as a dogleg shunt 92. Other implementations are possible.

Figure 14C:
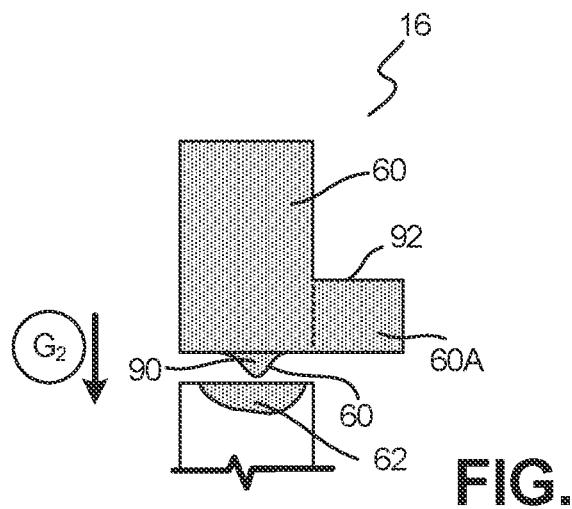
FIG. 14C is a further top view of the implementation of FIG. 14A showing bridging of the gap and initial saturation of the second substrate.

In the implementations of FIGS. 14A-14C, a second substrate portion 16B is disposed "below" the first 16A relative to gravity (G), and this second portion 16B can act as an overflow reservoir. As best shown in FIGS. 14A-14B, the initial flow of fluid 60 is in the direction of gravity (shown by reference arrow G). However, in these implementations, when the fluid reaches the gap 90, that additional fluid 60A will begin to flow laterally (shown by reference arrow L) into the shunt 92. As shown in FIG. 14C, upon saturation of the first portion 16A and the shunt 92 with fluid 60, 60A a fluidic bridge 61 can cross the gap 90, so as to transfer additional fluid 60 into the second portion 16B (reference arrow $G_2$). In these implementations, the fluid 60A contained in the shunt 92 is therefore able to be static, such that additional fluid entering the substrate passes through the passes through the first substrate portion 16A—bypassing the shunt 92, when a specified volume of fluid 60A is being held statically—so as to bridge 61 and enters the second substrate portion 16B via the gap 90. These implementations can be used to collect blood 60A in the shunt 92 to present fluid exchanges or to soak excess fluid and control the fluid volume in the first substrate. As would be apparent to a skilled artisan, many configurations of these elements are possible.

Figure 15A:
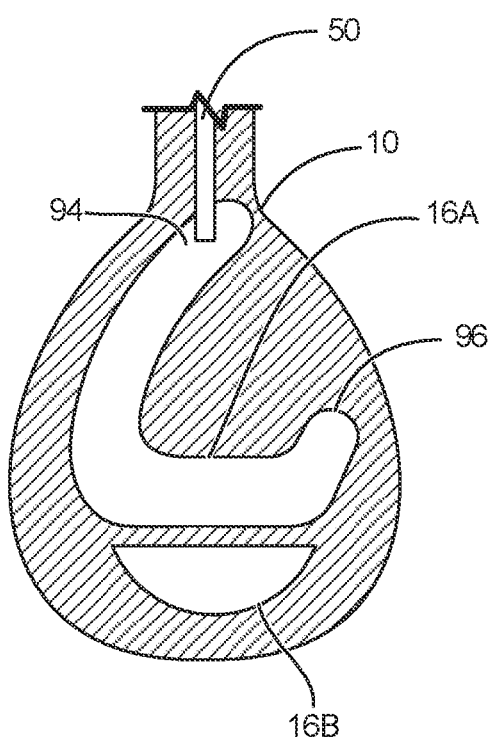
FIG. 15A is a top view of a substrate embodiment showing a method for plasma separation on the substrate in a cartridge with the ability to control the volume of plasma separated.
Figure 15B:
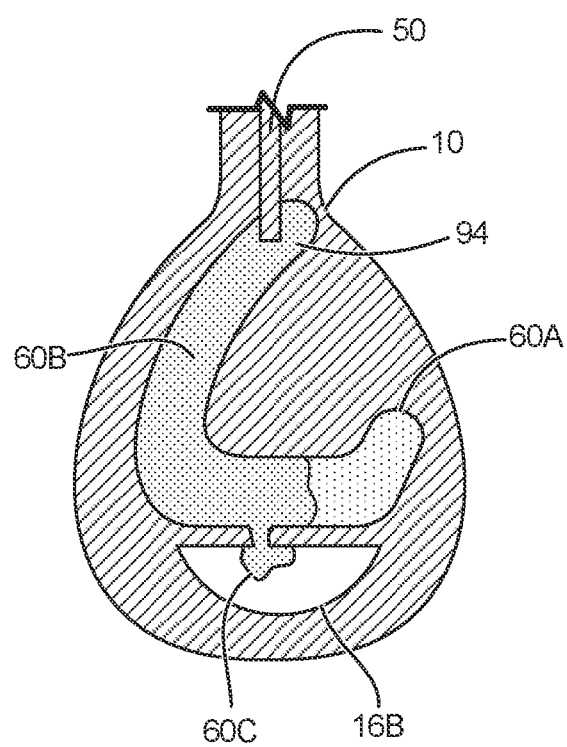
FIG. 15B is a further view of the implementation of FIG. 15A, showing the saturation of the substrate with blood and plasma.

An alternate bridging substrate 16 is shown in the implementations of FIGS. 15A-15B. In these implementations, the use of a separate second portion 16B can provide overflow collection during the collection of plasma 60A. In these implementations, the first portion 16A is comprised of separation paper 16A that preferentially allows plasma 60A flow. In these implementations, as fluid 60 progresses from the first substrate end 94 to a second substrate end 96, blood 60B is separated from plasma 60A, in that plasma 60A saturates the second end 96 prior to the arrival of blood 60B. In these implementations, by controlling the shape of the first substrate, such as by using a curved, or "hooked" configuration (generally at 19), the second substrate end 96 can be selectively saturated with plasma 60A, so that plasma 60A is retained in that second end 96, while blood 60B remains in the first end longer and then selectively bridges 60C to the second substrate portion 16B as needed.

Various alternative substrate configurations are shown in the implementations of FIGS. 16A-16C. In various implementations, the arrangement of the substrates and selection of substrate type and shape can allow the individual substrates to perform a variety of modular, or networked features and actions on blood flowing into the collector. For example, in various implementations, the substrates can preferentially absorb blood, plasma or other fluids; transfer blood or other fluids with minimal volumes absorbed; apply a reagent or other treatment to the blood or fluid and/or filter the fluid blood. Additional features are also contemplated.

In FIG. 16A, three substrates 16A, 16B, 16C are provided, with various reagents 80A, 80B being incorporated into the downstream substrates 16B, 16C, as has been previously described above. Importantly, these networks of substrates can be modular in nature, and incorporate any number of variations depending on the assays of interest. In various implementations, the substrate pore size can be used to control the capillary pressure or force between the various substrates and thereby control fluid flow and saturation.

For example, in FIG. 16B, a network is provided comprising three substrates 16A, 16B, 16C. In this implementation, the second substrate 16B is an elongate paper channel 16B of separation paper, as was discussed in relation to FIG. 15A-B. Accordingly, in this implementation, after the first substrate 16A fills with fluid 60, the fluid enters the separation channel 16B. In the separation channel 16B, the plasma 60A proceeds faster than whole blood 60, such that the third substrate 16C is selectively saturated with plasma 60A while the whole blood 60 is retained upstream, in the first substrate 16A and the portion of the channel 16B adjacent the first substrate.

In the implementation of FIG. 16C, an additional overflow substrate 16D is provided and disposed adjacent to the first 16A. In this implementation, excess blood 60 can be directed into the overflow substrate while plasma saturates the third substrate 16C. As would be apparent, myriad additional combinations are possible.

Although the disclosure has been described with reference to preferred embodiments, persons skilled in the art will recognize that changes may be made in form and detail without departing from the spirit and scope of the disclosed apparatus, systems and methods.

We claim:

1. A system for collecting blood from a subject, the system comprising:
   a blood collection device sized and shaped to be positioned against skin of the subject, wherein the blood collection device is actuatable to puncture the skin of the subject and to collect blood from the subject;
   a collection cartridge having a first end portion and a second end portion opposite the first portion, wherein the collection cartridge defines a lumen extending at least partially between the first and second end portions, wherein the first end portion includes a connector sized and shaped to be releasably coupled to the blood collection device to create a hermetic seal with the blood collection device and to receive a flow of the blood from the blood collection device;
   multiple substrates positioned within the lumen, wherein the substrates are spaced apart from one another and out of contact with one another, wherein the substrates each include a first end portion and a second end portion, wherein the substrates are each formed from a porous material and collectively have a fixed saturation volume, wherein the first end portion of each of the substrates is positioned proximate to the connector to receive the flow of the blood such that the each of the substrates sequentially fills with and stores the blood in a direction extending from the first end portion toward the second end portion of the corresponding one of the substrates; and
   an overflow reservoir positioned in the lumen proximate to the second end portion of each of the substrates, wherein the overflow reservoir is positioned to collect the flow of the blood after the substrates have sequentially filled to and stored the fixed saturation volume.

2. The system of claim 1 wherein the overflow reservoir is an absorbent pad.

3. The system of claim 1 wherein the overflow reservoir has a fixed saturation volume that is greater than the fixed saturation volume of the substrates.

4. The system of claim 1 wherein the porous material is a fibrous matrix.

5. The system of claim 1 wherein the porous material is paper.

6. The system of claim 1 wherein the connector has a circular cross sectional-shape along a plane extending perpendicular to a direction extending from the first end portion toward the second end portion of the collection cartridge.

7. The system of claim 1 wherein the substrate has a rectangular shape.

8. The system of claim 1 wherein the substrates are suspended within the lumen.

9. The system of claim 1, further comprising a gasket configured to seal the interface between the connector and blood collection device to create the hermetic seal.

10. The system of claim 1 wherein the substrates are configured to wick the blood in the direction extending from the first end portion toward the second end portion of the substrate.

11. A cartridge for collecting a bodily fluid, the cartridge comprising:
    a housing having a first end portion and a second end portion opposite the first portion, wherein the housing defines a lumen extending at least partially between the first and second end portions, and wherein the first end portion is positioned to receive a flow of the bodily fluid;

multiple substrates positioned within the lumen, wherein the substrates are spaced apart from one another and out of contact with one another, wherein the substrates each include a first end portion and a second end portion, wherein the substrates are each formed from a porous material and collectively have a fixed saturation volume, and wherein the first end portion of each of the substrates is positioned proximate to the first end portion of the housing to receive the flow of the bodily fluid and to sequentially fill with and store the bodily fluid in a direction extending from the first end portion toward the second end portion of the corresponding one of the substrates; and an overflow reservoir positioned in the lumen proximate the second end portion of the substrate, wherein the overflow reservoir is positioned to absorb the flow of the bodily fluid after the substrates have sequentially filled with and stored the fixed saturation volume.

12. The cartridge of claim 11 wherein the overflow reservoir is an absorbent pad having a fixed saturation volume that is greater than the fixed saturation volume of the substrate.

13. The cartridge of claim 11 wherein the porous material is a fibrous matrix.

14. The cartridge of claim 11 wherein the porous material is paper and wherein the substrate has a rectangular shape.

15. The cartridge of claim 11 wherein the substrates are at least partially suspended within the lumen, and wherein the substrates are each configured to wick the blood in the direction extending from the first end portion toward the second end portion of the corresponding one of the substrates.

16. The cartridge of claim 11 wherein the housing has a rectangular shape.

17. The cartridge of claim 11 wherein the first end portion of the cartridge includes a connector sized and shaped to be releasably coupled to a bodily fluid collection device to create a hermetic seal with the bodily fluid collection device and to receive the flow of the bodily fluid from the bodily fluid collection device.

18. A cartridge for collecting a bodily fluid, the cartridge comprising:
a housing having a first end portion and a second end portion opposite the first portion, wherein the housing defines a lumen extending at least partially between the first and second end portions, and wherein the first end portion includes a connector sized and shaped to be releasably coupled to a blood collection device to receive a flow of the bodily fluid from the blood collection device;
multiple porous substrates positioned within the lumen, wherein the substrates are spaced apart from one another and out of contact with one another, wherein the porous substrates are each positioned to sequentially fill with and store the bodily fluid in a direction extending from the first end portion toward the second end portion of the housing, and wherein the substrates collectively have a fixed saturation volume; and
an overflow reservoir positioned proximate the second end portion of the housing, wherein the overflow reservoir is positioned to absorb any of the bodily fluid exceeding the fixed saturation volume of the substrates.

19. The cartridge of claim 18 wherein the overflow reservoir has a fixed saturation volume that is greater than the fixed saturation volume of the substrates.

* * * * *